US012707153B2

(12) United States Patent
Kojima

(10) Patent No.: US 12,707,153 B2
(45) Date of Patent: Aug. 11, 2026

(54) MEDICAL CONTROL DEVICE AND MEDICAL OBSERVATION SYSTEM

(71) Applicant: Sony Olympus Medical Solutions Inc., Tokyo (JP)

(72) Inventor: Koji Kojima, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 18/677,966

(22) Filed: May 30, 2024

(65) Prior Publication Data

US 2024/0414442 A1 Dec. 12, 2024

(30) Foreign Application Priority Data

Jun. 9, 2023 (JP) ................................ 2023-095619

(51) Int. Cl.

| | |
|---|---|
| ***H04N 23/74*** | (2023.01) |
| ***A61B 1/00*** | (2006.01) |
| ***A61B 1/06*** | (2006.01) |
| ***H04N 23/13*** | (2023.01) |
| ***H04N 23/72*** | (2023.01) |
| ***H04N 23/73*** | (2023.01) |

(52) U.S. Cl.

CPC ......... *H04N 23/74* (2023.01); *A61B 1/00006* (2013.01); *A61B 1/0655* (2022.02); *H04N 23/13* (2023.01); *H04N 23/72* (2023.01); *H04N 23/73* (2023.01)

(58) Field of Classification Search

CPC ........ H04N 23/74; H04N 23/13; H04N 23/72; H04N 23/73; A61B 1/00006; A61B 1/0655; A61B 1/00009; A61B 1/00186; A61B 1/043; A61B 1/045; A61B 1/0638

See application file for complete search history.

(56) References Cited

U.S. PATENT DOCUMENTS

2015/0035970 A1* 2/2015 Brumbaugh ....... G01N 21/9054 348/93
2020/0081235 A1* 3/2020 Takahashi .......... G02B 21/0012
2021/0290037 A1* 9/2021 Michihata .......... A61B 1/00006
2022/0166912 A1* 5/2022 Kojima .................. A61B 1/043
2022/0257097 A1* 8/2022 Shimomura ......... A61B 1/0638

FOREIGN PATENT DOCUMENTS

JP 2020-116148 A 8/2020

* cited by examiner

*Primary Examiner* — Nasim N Nirjhar
(74) *Attorney, Agent, or Firm* — XSENSUS LLP

(57) ABSTRACT

A medical control device includes: a dimming control unit configured to control an operation of a light source device configured to emit first light and second light, and adjust light amounts of the first and the second light; and an imaging control unit configured to control an operation of an imaging device including at least one imaging element, irradiate an observation target with the first light to capture return light of the first light via the observation target to generate a first captured image, and irradiate the observation target with the second light to capture return light of the second light via the observation target to generate a second captured image. The imaging control unit is configured to execute changing an exposure period of the imaging element, and discarding image information generated by the imaging element according to light reception in a partial period of the exposure period.

20 Claims, 17 Drawing Sheets

1/60 [s]
(a)
(b) Th
(c)
(d) Th

1/30 [s]
Ar1
Ar2
1/30 [s]
(a)
(b) Th
(c)
(d) Th

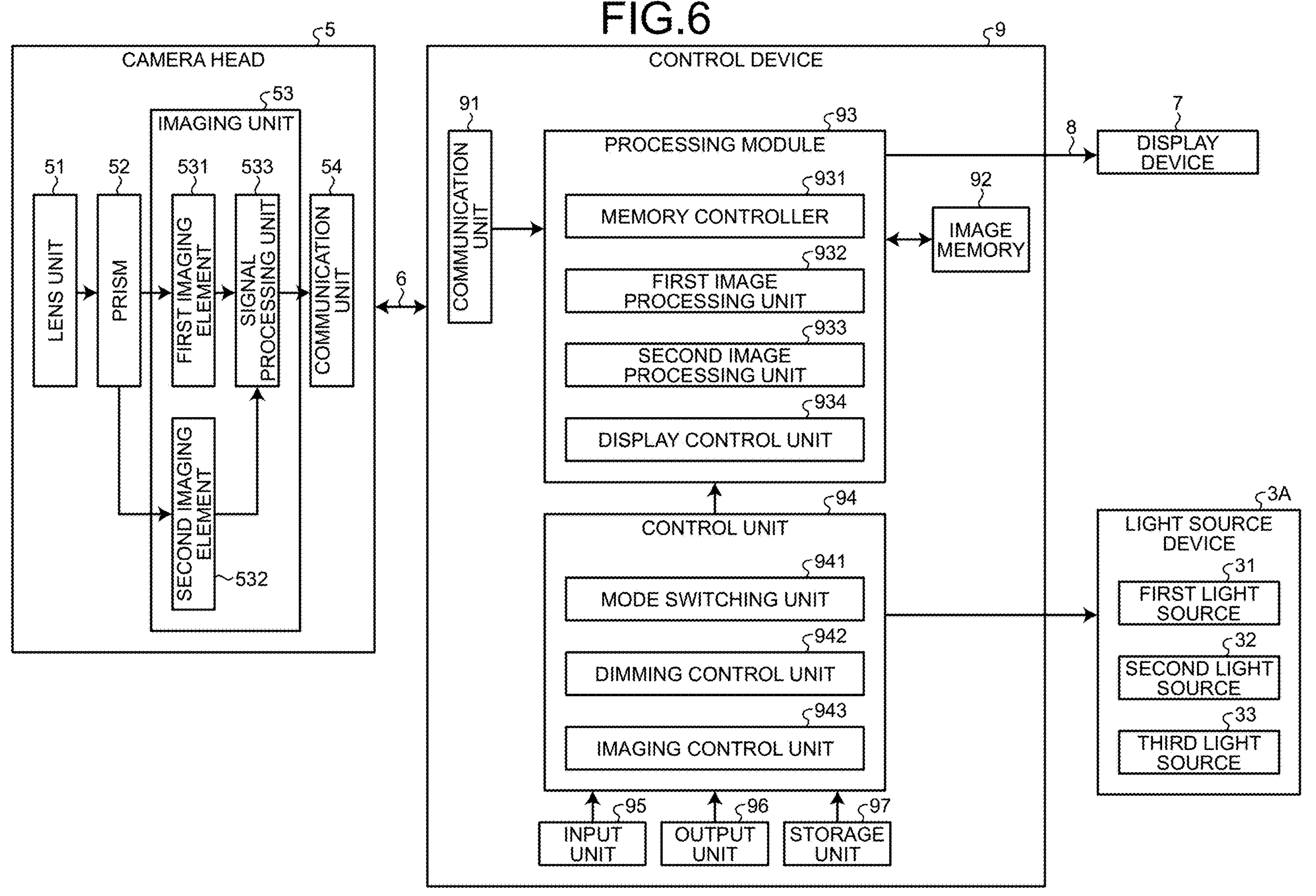
FIG.6
CAMERA HEAD
5
IMAGING UNIT
53
51
LENS UNIT
52
PRISM
531
FIRST IMAGING ELEMENT
533
SIGNAL PROCESSING UNIT
54
COMMUNICATION UNIT
SECOND IMAGING ELEMENT
532
6
CONTROL DEVICE
9
91
COMMUNICATION UNIT
PROCESSING MODULE
93
931
MEMORY CONTROLLER
932
FIRST IMAGE PROCESSING UNIT
933
SECOND IMAGE PROCESSING UNIT
934
DISPLAY CONTROL UNIT
92
IMAGE MEMORY
CONTROL UNIT
94
941
MODE SWITCHING UNIT
942
DIMMING CONTROL UNIT
943
IMAGING CONTROL UNIT
95
INPUT UNIT
96
OUTPUT UNIT
97
STORAGE UNIT
8
7
DISPLAY DEVICE
3A
LIGHT SOURCE DEVICE
31
FIRST LIGHT SOURCE
32
SECOND LIGHT SOURCE
33
THIRD LIGHT SOURCE 1/30 [s]
1/60 [s]
1/30 [s]
(a)
(b) Th
(c)
(d) Th

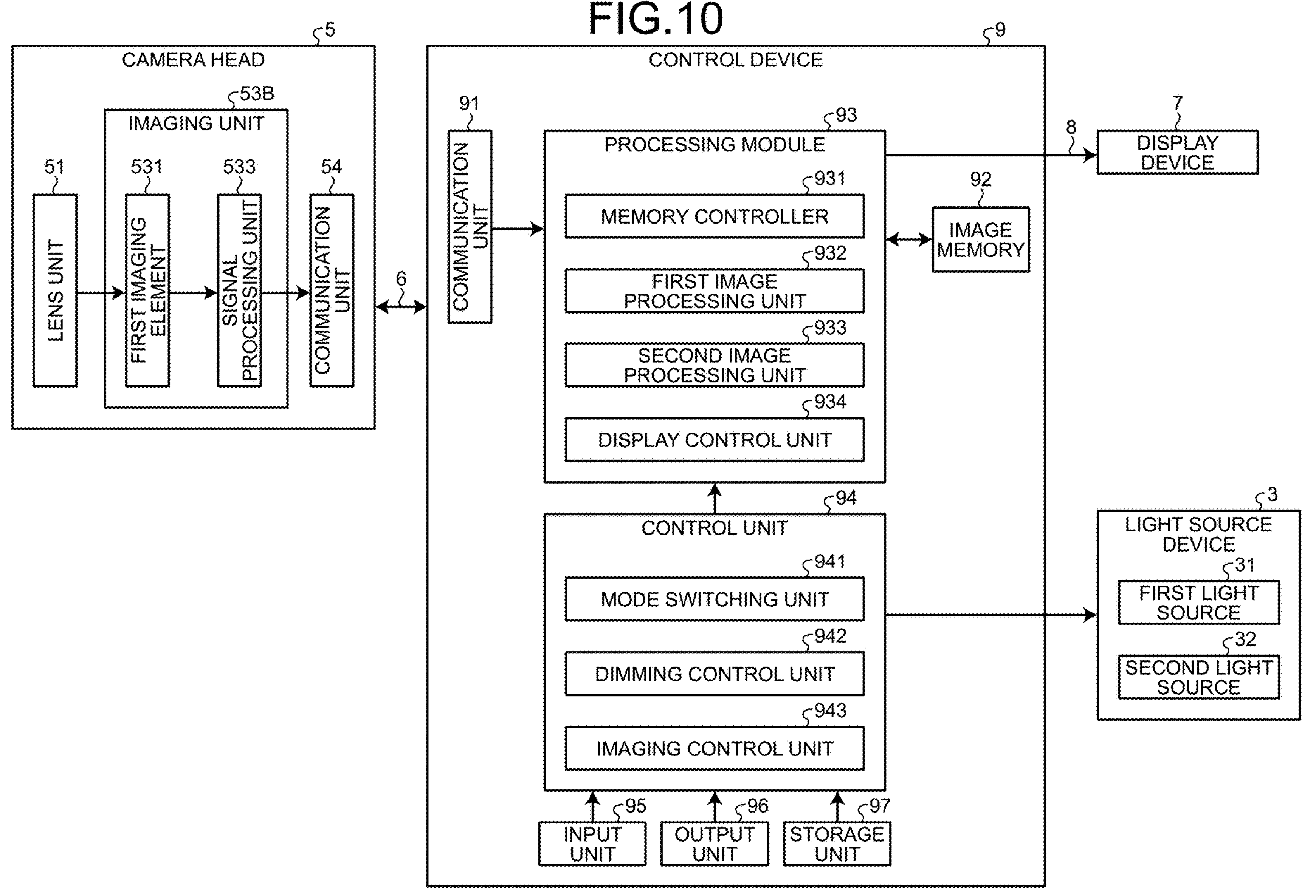
FIG.10
CAMERA HEAD
5
IMAGING UNIT
53B
LENS UNIT
51
FIRST IMAGING ELEMENT
531
SIGNAL PROCESSING UNIT
533
COMMUNICATION UNIT
54
6
CONTROL DEVICE
9
COMMUNICATION UNIT
91
PROCESSING MODULE
93
MEMORY CONTROLLER
931
FIRST IMAGE PROCESSING UNIT
932
SECOND IMAGE PROCESSING UNIT
933
DISPLAY CONTROL UNIT
934
IMAGE MEMORY
92
CONTROL UNIT
94
MODE SWITCHING UNIT
941
DIMMING CONTROL UNIT
942
IMAGING CONTROL UNIT
943
INPUT UNIT
95
OUTPUT UNIT
96
STORAGE UNIT
97
8
DISPLAY DEVICE
7
LIGHT SOURCE DEVICE
3
FIRST LIGHT SOURCE
31
SECOND LIGHT SOURCE
32

FIG.11

(a)
1/30 [s]
1/30 [s]
WLI FIELD
IR FIELD
WLI FIELD
IR FIELD
WLI FIELD (b) Th
TE1
TE1
TE1

(a)
1/30 [s]
1/30 [s]
WLI FIELD
IR FIELD
WLI FIELD
IR FIELD
WLI FIELD
Ar1
Ar2

WLI FIELD

IR FIELD

WLI FIELD

IR FIELD

WLI FIELD (b) Th

TE1

TE1

TE1

(c) Th

TRB

TE2

TRA

TRB

TE2

TRA

WLI FIELD

IR FIELD

Ar1'

Ar2'

WLI FIELD

IR FIELD

WLI FIELD

TE1

TE1

TE1

(b) Th (c) Th

TRB

TE2

TRA

TRB

TE2

TRA

FIG.15

MEDICAL CONTROL DEVICE AND MEDICAL OBSERVATION SYSTEM

CROSS-REFERENCE TO RELATED APPLICATION

This application claims priority from Japanese Application No. 2023-095619, filed on Jun. 9, 2023, the contents of which are incorporated by reference herein in its entirety.

BACKGROUND

The present disclosure relates to a medical control device and a medical observation system.

In the related art, a medical observation system that captures an observation target in a living body or the like and observes the observation target is known (see, for example, JP 2020-116148 A).

The medical observation system described in JP 2020-116148 A generates first and second captured images described below.

The first captured image is a captured image in which the observation target is irradiated with first light such as special light, and return light of the first light via the observation target is captured.

The second captured image is a captured image obtained by capturing the return light of the second light via the observation target when the observation target is irradiated with the second light such as normal light.

SUMMARY

Meanwhile, when brightness of the first and second captured images is adjusted, it is conceivable to execute dimming control of a light source device that emits the first and second lights as described below.

The light amount of the second light is adjusted based on the brightness of the specific region in the second captured image to adjust the second captured image to the reference brightness. Furthermore, the light amount of the first light is adjusted in accordance with the adjustment of the light amount of the second light while maintaining a state in which a ratio between the light amount of the first light and the light amount of the second light is a specific ratio, and the brightness of the first captured image is adjusted.

However, when the dimming control is executed while maintaining a state in which the ratio between the light amount of the first light and the light amount of the second light is a specific ratio, there is a problem that the dimming control of the light source device exceeds a range in which the dimming control of the light source device can be performed, and the dimming control of the light source device cannot be appropriately performed.

There is a need for a medical control device and a medical observation system that are able to perform dimming control of the light source device appropriately.

According to one aspect of the present disclosure, there is provided a medical control device including: a dimming control unit configured to control an operation of a light source device configured to emit first light and second light having a wavelength band different from a wavelength band of the first light, and adjust a light amount of the first light and a light amount of the second light; and an imaging control unit configured to control an operation of an imaging device including at least one imaging element, irradiate an observation target with the first light to capture return light of the first light via the observation target to generate a first captured image, and irradiate the observation target with the second light to capture return light of the second light via the observation target to generate a second captured image, wherein the imaging control unit is configured to execute first processing of changing an exposure period of the imaging element, and second processing of discarding image information generated by the imaging element according to light reception in a partial period of the exposure period.

According to another aspect of the present disclosure, there is provided a medical observation system including: a light source device configured to emit first light and second light having a wavelength band different from a wavelength band of the first light; an imaging device including at least one imaging element, the imaging device being configured to irradiate an observation target with the first light to capture return light of the first light via the observation target to generate a first captured image, and irradiate the observation target with the second light to capture return light of the second light via the observation target to generate a second captured image; and a control device configured to control operations of the light source device and the imaging device, the control device including a dimming control unit configured to control an operation of the light source device and adjusts a light amount of the first light and a light amount of the second light, and an imaging control unit configured to control an operation of the imaging device, and execute first processing of changing an exposure period of the imaging element, and second processing of discarding image information generated by the imaging element according to light reception in a partial period of the exposure period.

BRIEF DESCRIPTION OF THE DRAWINGS

FIG. 6 is a diagram illustrating a first modification of the embodiment;

FIG. 10 is a diagram for describing a third modification of the embodiment;

FIG. 11 is a diagram for describing the third modification of the embodiment;

FIG. 12 is a diagram for describing the third modification of the embodiment;

FIG. 13 is a diagram for describing a fourth modification of the embodiment;

FIG. 14 is a diagram for describing the fourth modification of the embodiment;

FIG. 15 is a diagram for describing a fifth modification of the embodiment;

DETAILED DESCRIPTION

Figure 1:
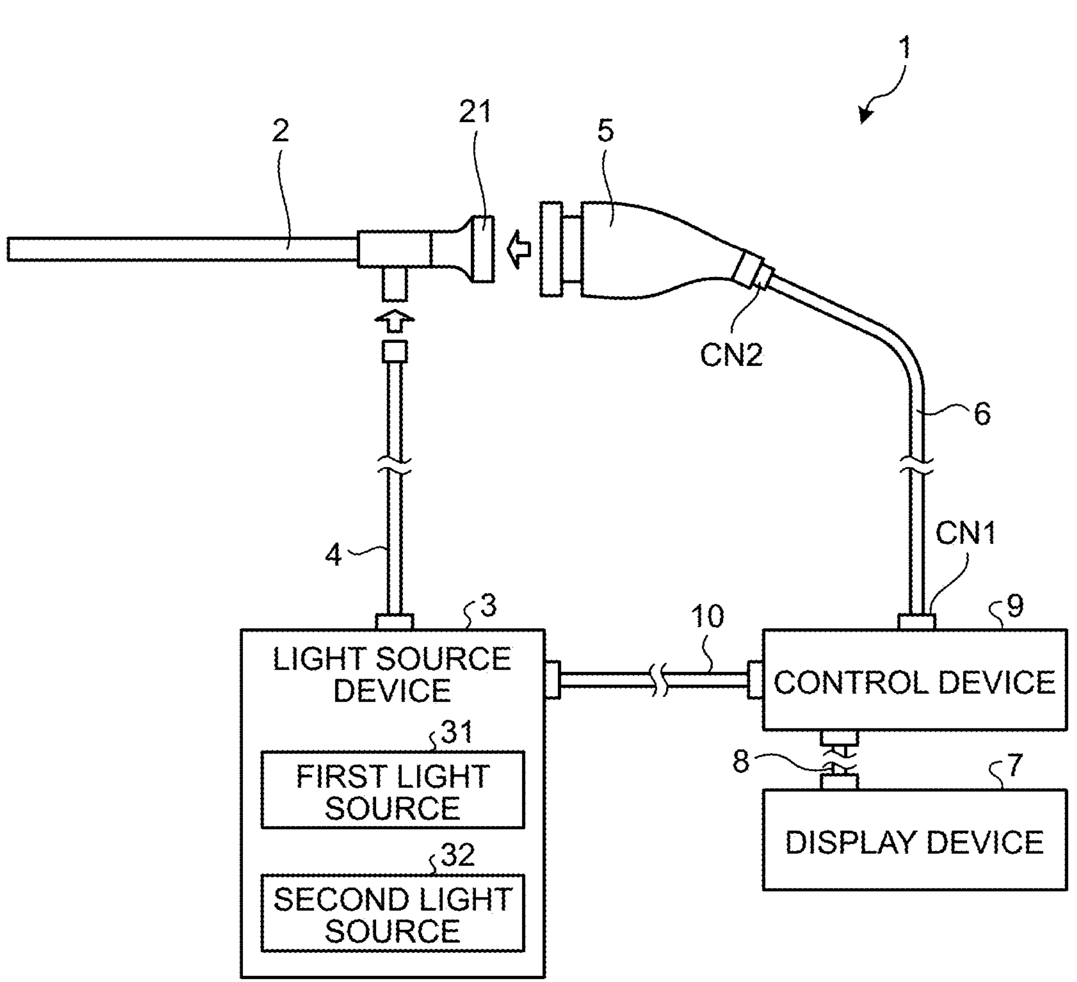
FIG. 1 is a diagram illustrating a configuration of a medical observation system according to an embodiment.

Hereinafter, a mode (hereinafter, embodiment) for carrying out the present disclosure will be described with reference to the drawings. Note that the present disclosure is not limited by the embodiment described below. Furthermore, in the description of the drawings, the same portions are denoted by the same reference numerals.

Schematic Configuration of Medical Observation System

FIG. 1 is a diagram illustrating a configuration of a medical observation system 1 according to a first embodiment.

The medical observation system 1 is a system that is used in a medical field and observes the inside of a living body (observation target) that is a subject. As illustrated in FIG. 1, the medical observation system 1 includes an insertion unit 2, a light source device 3, a light guide 4, a camera head 5, a first transmission cable 6, a display device 7, a second transmission cable 8, a control device 9, and a third transmission cable 10.

In the present embodiment, the insertion unit 2 includes a rigid endoscope. That is, the insertion unit 2 has an elongated shape that is entirely rigid or partially soft and rigid in the remaining portion, and is inserted into the living body. An optical system configured to use one or a plurality of lenses and condense light from a subject is provided in the insertion unit 2.

The light source device 3 is connected to one end of the light guide 4, and supplies light to irradiate the inside of the living body to the one end of the light guide 4 under the control of the control device 9. As illustrated in FIG. 1, the light source device 3 includes a first light source 31 and a second light source 32.

The first light source 31 emits first light in a first wavelength band. In the present embodiment, the first light source 31 includes a semiconductor laser that emits near-infrared excitation light (first light) in a near-infrared wavelength band.

The near-infrared excitation light emitted by the first light source 31 is excitation light that excites a fluorescent substance such as indocyanine green. When excited by the near-infrared excitation light, the fluorescent substance such as indocyanine green emits fluorescence (return light of the near-infrared excitation light) having a central wavelength on a longer wavelength side than a central wavelength of a wavelength band of the near-infrared excitation light.

The second light source 32 emits second light in a second wavelength band different from the first wavelength band. In the present embodiment, the second light source 32 includes a light emitting diode (LED) that emits white light (second light).

In the present embodiment, the light source device 3 is configured separately from the control device 9, but the present disclosure is not limited thereto, and a configuration provided in the same casing as the control device 9 may be adopted.

One end of the light guide 4 is detachably connected to the light source device 3, and the other end is detachably connected to the insertion unit 2. Then, the light guide 4 transmits light (near-infrared excitation light or white light) supplied from the light source device 3 from one end to the other end, and supplies the light to the insertion unit 2. The light (near-infrared excitation light or white light) supplied to the insertion unit 2 is emitted from the distal end of the insertion unit 2 and emitted into the living body. When the near-infrared excitation light is emitted into the living body, the near-infrared excitation light reflected in the living body and a fluorescent substance such as indocyanine green accumulated at a lesion in the living body are excited, and fluorescence emitted from the fluorescent substance is collected by the optical system in the insertion unit 2. Hereinafter, for convenience of description, the near-infrared excitation light and the fluorescence collected by the optical system in the insertion unit 2 will be referred to as a first subject image. Furthermore, in a case where the white light is emitted into the living body, the white light reflected in the living body is condensed by the optical system in the insertion unit 2. Note that, hereinafter, for convenience of description, the white light condensed by the optical system in the insertion unit 2 is referred to as a second subject image.

The camera head 5 corresponds to an imaging device according to the present disclosure. The camera head 5 is detachably connected to the proximal end (eyepiece unit 21 (FIG. 1)) of the insertion unit 2. Then, under the control of the control device 9, the camera head 5 captures the first subject image (return light (near-infrared excitation light and fluorescence) of the near-infrared excitation light through the observation target) and the second subject image (return light (white light) of the white light through the observation target) condensed by the insertion unit 2 to generate an image signal (hereinafter, referred to as a captured image.).

Note that a detailed configuration of the camera head will be described in "Configuration of Camera Head" described later.

One end of the first transmission cable 6 is detachably connected to the control device 9 via a connector CN1 (FIG. 1), and the other end thereof is detachably connected to the camera head 5 via a connector CN2 (FIG. 1). Then, the first transmission cable 6 transmits the captured image and the like output from the camera head 5 to the control device 9, and transmits a control signal, a synchronization signal, a clock, power, and the like output from the control device 9 to the camera head 5.

Note that, in the transmission of the captured image and the like from the camera head 5 to the control device 9 via the first transmission cable 6, the captured image and the like may be transmitted as an optical signal or may be transmitted as an electric signal. The same applies to transmission of a control signal, a synchronization signal, and a clock from the control device 9 to the camera head 5 via the first transmission cable 6.

The display device 7 includes a display using liquid crystal, organic electro luminescence (EL), or the like, and displays an image based on a video signal from the control device 9 under the control of the control device 9.

One end of the second transmission cable 8 is detachably connected to the display device 7, and the other end is detachably connected to the control device 9. Then, the second transmission cable 8 transmits the video signal processed by the control device 9 to the display device 7.

The control device 9 corresponds to a medical control device according to the present disclosure. The control device 9 includes a central processing unit (CPU), a field-programmable gate array (FPGA), and the like, and integrally controls operations of the light source device 3, the camera head 5, and the display device 7. Note that a detailed configuration of the control device 9 will be described in "Configuration of Control Device" described later.

One end of the third transmission cable 10 is detachably connected to the light source device 3, and the other end thereof is detachably connected to the control device 9. Then, the third transmission cable 10 transmits the control signal from the control device 9 to the light source device 3.

Configuration of Camera Head

Next, a configuration of the camera head 5 will be described.

Figure 2:
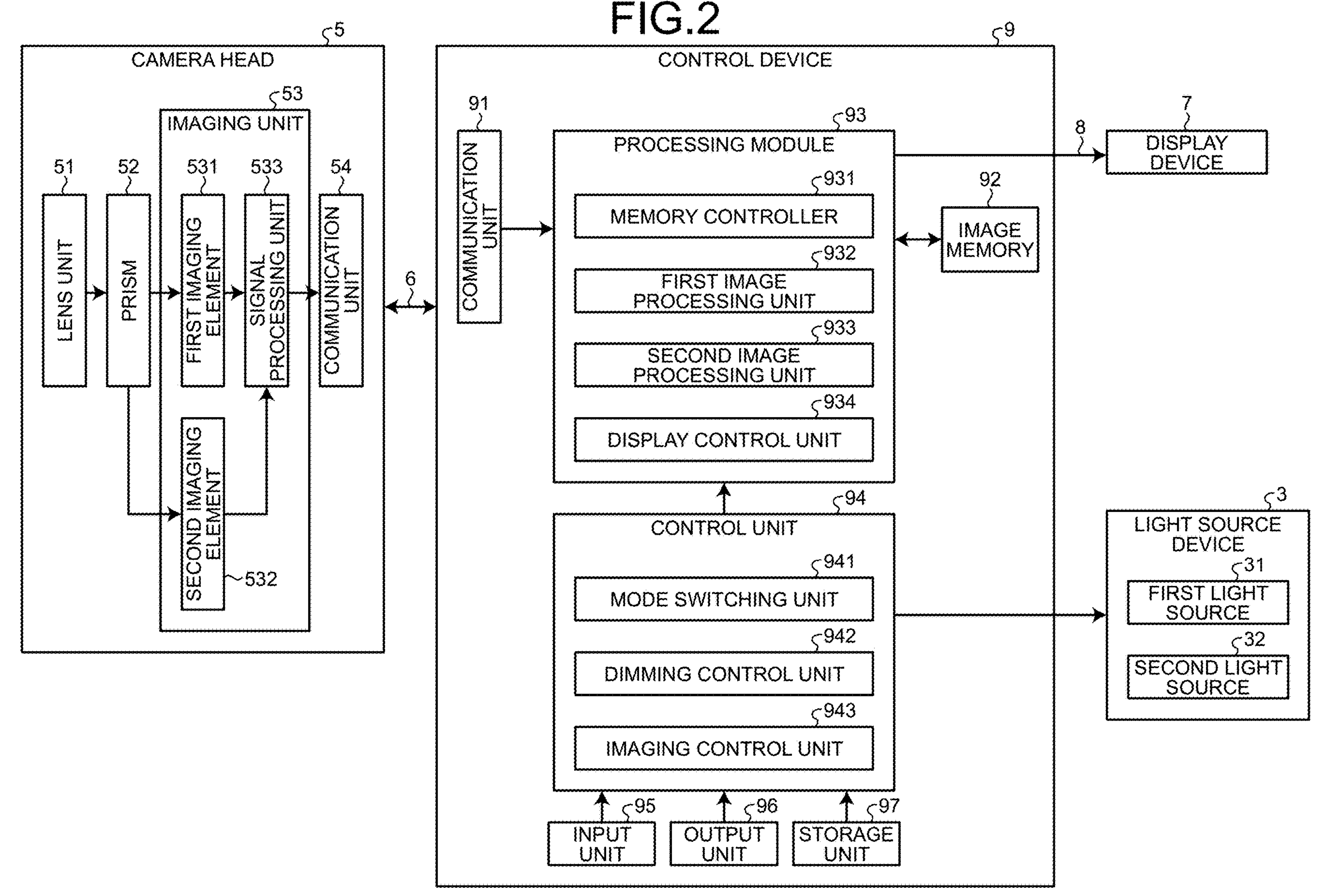
FIG. 2 is a block diagram illustrating a configuration of a camera head and a control device.

FIG. 2 is a block diagram illustrating a configuration of the camera head 5 and the control device 9.

As illustrated in FIG. 2, the camera head 5 includes a lens unit 51, a prism 52, an imaging unit 53, and a communication unit 54.

The lens unit 51 includes one or a plurality of lenses. Then, the lens unit 51 forms the first subject image (near-infrared excitation light and fluorescence) condensed by the insertion unit 2 on the imaging surface of the first imaging element 531 (FIG. 2), and forms the second subject image (white light) condensed by the insertion unit 2 on the imaging surface of the second imaging element 532 (FIG. 2).

The prism 52 separates the first subject image (near-infrared excitation light and fluorescence) and the second subject image (white light) through the lens unit 51. Then, the prism 52 advances the first subject image (near-infrared excitation light and fluorescence) toward the first imaging element 531. Furthermore, the prism 52 advances the second subject image (white light) toward the second imaging element 532.

The imaging unit 53 captures the inside of the living body under the control of the control device 9. As illustrated in FIG. 2, the imaging unit 53 includes the first imaging element 531, the second imaging element 532, and a signal processing unit 533.

The first and second imaging elements 531 and 532 receive a subject image and convert the subject image into an electric signal (analog signal). In the present embodiment, each of the first and second imaging elements 531 and 532 includes a complementary metal oxide semiconductor (CMOS) which is a rolling shutter type imaging element in which a plurality of pixels is two-dimensionally arranged in units of horizontal lines.

Here, although not specifically illustrated, the first imaging element 531 includes an invalid region that is not electrically guaranteed, an optical black region (OB region), and an effective pixel region that converts the first subject image formed by the lens unit 51 into an imaging signal and outputs the imaging signal. Note that the second imaging element 532 similarly includes an invalid region, an optical black region (OB region), and an effective pixel region.

Then, the first imaging element 531 captures the first subject image (near-infrared excitation light and fluorescence) through the prism 52 under the control of the control device 9. Hereinafter, for convenience of description, a captured image generated by capturing the first subject image (near-infrared excitation light and fluorescence) by the first imaging element 531 is referred to as a fluorescence image.

Note that an excitation light cut filter that removes only at least a part of the near-infrared excitation light traveling toward the first imaging element 531 may be disposed on the front stage side of the optical path of the first imaging element 531.

Furthermore, the second imaging element 532 captures the second subject image (white light) via the prism 52 under the control of the control device 9. Hereinafter, for convenience of description, a captured image generated by capturing the second subject image (white light) by the second imaging element 532 is referred to as a normal light image.

Note that the number of pixels of the fluorescence image and the number of pixels of the normal light image may be different from each other or may be the same.

Under the control of the control device 9, the signal processing unit 533 performs signal processing on the captured images (analog signals) generated by the first and second imaging elements 531 and 532 and outputs the captured images (digital signals).

For example, the signal processing unit 533 performs processing of removing reset noise, processing of multiplying an analog gain for amplifying the analog signal, and signal processing such as A/D conversion on the captured images (analog signals) generated by the first and second imaging elements 531 and 532.

The communication unit 54 functions as a transmitter that transmits the captured images sequentially output from the imaging unit 53 to the control device 9 via the first transmission cable 6. The communication unit 54 includes, for example, a high-speed serial interface that communicates a captured image with the control device 9 via the first transmission cable 6 at a transmission rate of 1 Gbps or more.

Note that the communication unit 54 may alternately transmit the fluorescence image and the normal light image to the control device 9, or may simultaneously transmit the fluorescence image and the normal light image. In the following description, it is assumed that the fluorescence image and the normal light image are alternately transmitted to the control device 9.

Configuration of Control Device

Next, a configuration of the control device 9 will be described with reference to FIG. 2.

As illustrated in FIG. 2, the control device 9 includes a communication unit 91, an image memory 92, a processing module 93, a control unit 94, an input unit 95, an output unit 96, and a storage unit 97.

The communication unit 91 functions as a receiver that receives captured images sequentially transmitted from the camera head 5 (communication unit 54) via the first transmission cable 6. The communication unit 91 includes, for example, a high-speed serial interface that communicates captured images with the communication unit 54 at a transmission rate of 1 Gbps or more.

The image memory 92 includes, for example, a dynamic random access memory (DRAM) or the like. The image memory 92 can temporarily store a plurality of frames of captured images sequentially output from the camera head 5 (communication unit 54).

The processing module 93 processes the captured image sequentially transmitted from the camera head 5 (communication unit 54) and received by the communication unit 91 under the control of the control unit 94. As illustrated in FIG. 2, the processing module 93 includes a memory controller 931, a first image processing unit 932, a second image processing unit 933, and a display control unit 934.

The memory controller 931 controls writing of a captured image into the image memory 92 and reading of the captured image from the image memory 92. More specifically, the memory controller 931 writes the fluorescence image received by the communication unit 91 in the image memory 92, reads the fluorescence image from the image memory 92 at a specific timing, and inputs the fluorescence image to the first image processing unit 932. In addition, the memory controller 931 writes the normal light image received by the communication unit 91 in the image memory 92, reads the normal light image from the image memory 92 at a specific timing, and inputs the normal light image to the second image processing unit 933.

The first image processing unit 932 executes first image processing on the input fluorescence image.

Examples of the first image processing include optical black subtraction processing, white balance adjustment processing, demosaic processing, color correction matrix processing, gamma correction processing, YC processing of converting an RGB signal into a luminance chrominance signal (Y, Cb/Cr SIGNAL), gain adjustment, noise removal, and filter processing of enhancing a structure.

The second image processing unit 933 executes second image processing on the input normal light image.

Examples of the second image processing include optical black subtraction processing, white balance adjustment processing, demosaic processing, color correction matrix processing, gamma correction processing, YC processing of converting an RGB signal into a luminance chrominance signal (Y, Cb/Cr SIGNAL), gain adjustment, noise removal, and filter processing of enhancing a structure.

Note that the first and second image processing may be different from each other, or may be the same image processing.

Under the control of the control unit 94, the display control unit 934 generates a video signal for displaying the fluorescence image after the first image processing is executed by the first image processing unit 932 and the normal light image after the second image processing is executed by the second image processing unit 933. Then, the display control unit 934 outputs the video signal to the display device 7 via the second transmission cable 8.

The control unit 94 is realized by executing various programs stored in the storage unit 97 by a controller such as a CPU or a micro processing unit (MPU), and controls the operations of the light source device 3, the camera head 5, and the display device 7 and controls the entire operation of the control device 9. Note that the control unit 94 is not limited to the CPU or the MPU, and may be configured by an integrated circuit such as an application specific integrated circuit (ASIC) or an FPGA. As illustrated in FIG. 2, the control unit 94 has functions as a mode switching unit 941, a dimming control unit 942, and an imaging control unit 943.

The mode switching unit 941 switches a mode of the medical observation system 1 to either a normal observation mode or a fluorescence observation mode according to a user operation to an input unit (not illustrated) provided in the camera head 5 or a user operation to the input unit 95.

The normal observation mode is a mode in which only the normal light image out of the fluorescence image and the normal light image is generated and the normal light image is displayed on the display device 7.

In the normal observation mode, the control unit 94 turns on only the second light source 32 of the first and second light sources 31 and 32. Furthermore, the communication unit 54 sequentially transmits the normal light image generated by the imaging unit 53 to the communication unit 91. Furthermore, the processing module 93 executes second image processing on the normal light image received by the communication unit 91, generates a video signal for displaying the normal light image after execution of the second image processing, and outputs the video signal to the display device 7. As a result, the normal light image is displayed on the display device 7.

The fluorescence observation mode is a mode in which the fluorescence image and the normal light image are generated, and the fluorescence image and the normal light image (or a superimposed image obtained by superimposing the fluorescence image and the normal light image) are displayed on the display device 7.

In this fluorescence observation mode, the control unit 94 simultaneously turns on the first and second light sources 31 and 32. Furthermore, the communication unit 54 alternately transmits the fluorescence image and the normal light image generated by the imaging unit 53 to the communication unit 91. Furthermore, the processing module 93 executes image processing on each of the fluorescence image and the normal light image received by the communication unit 91, generates a video signal for displaying the fluorescence image and the normal light image (or the superimposed image obtained by superimposing the fluorescence image and the normal light image) after execution of the image processing, and outputs the video signal to the display device 7. As a result, the fluorescence image and the normal light image (or the superimposed image obtained by superimposing the fluorescence image and the normal light image) are displayed on the display device 7.

Functions of the dimming control unit 942 and the imaging control unit 943 will be described in "Functions of Dimming Control Unit and Imaging Control Unit" described later.

The input unit 95 is configured using an operation device such as a mouse, a keyboard, and a touch panel, and receives a user operation by a user such as an operator. Then, the input unit 95 outputs an operation signal corresponding to the user operation to the control unit 94.

The output unit 96 is configured using a speaker, a printer, or the like, and outputs various types of information.

The storage unit 97 stores a program executed by the control unit 94, information necessary for processing of the control unit 94, and the like.

Functions of Dimming Control Unit and Imaging Control Unit

Next, functions of the dimming control unit 942 and the imaging control unit 943 will be described.

Figure 3:
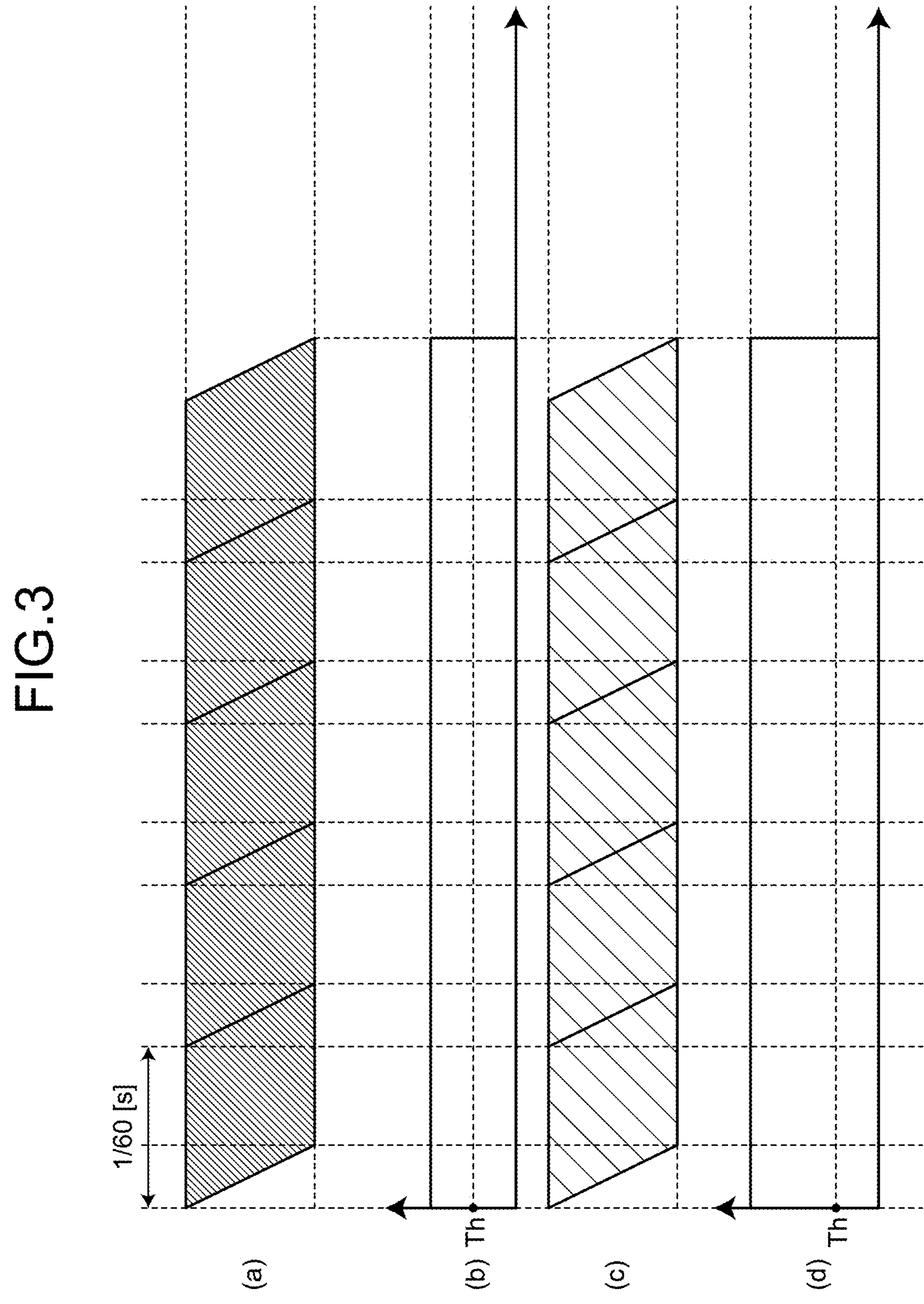
FIG. 3 is a diagram for describing functions of a dimming control unit and an imaging control unit.
Figure 4:
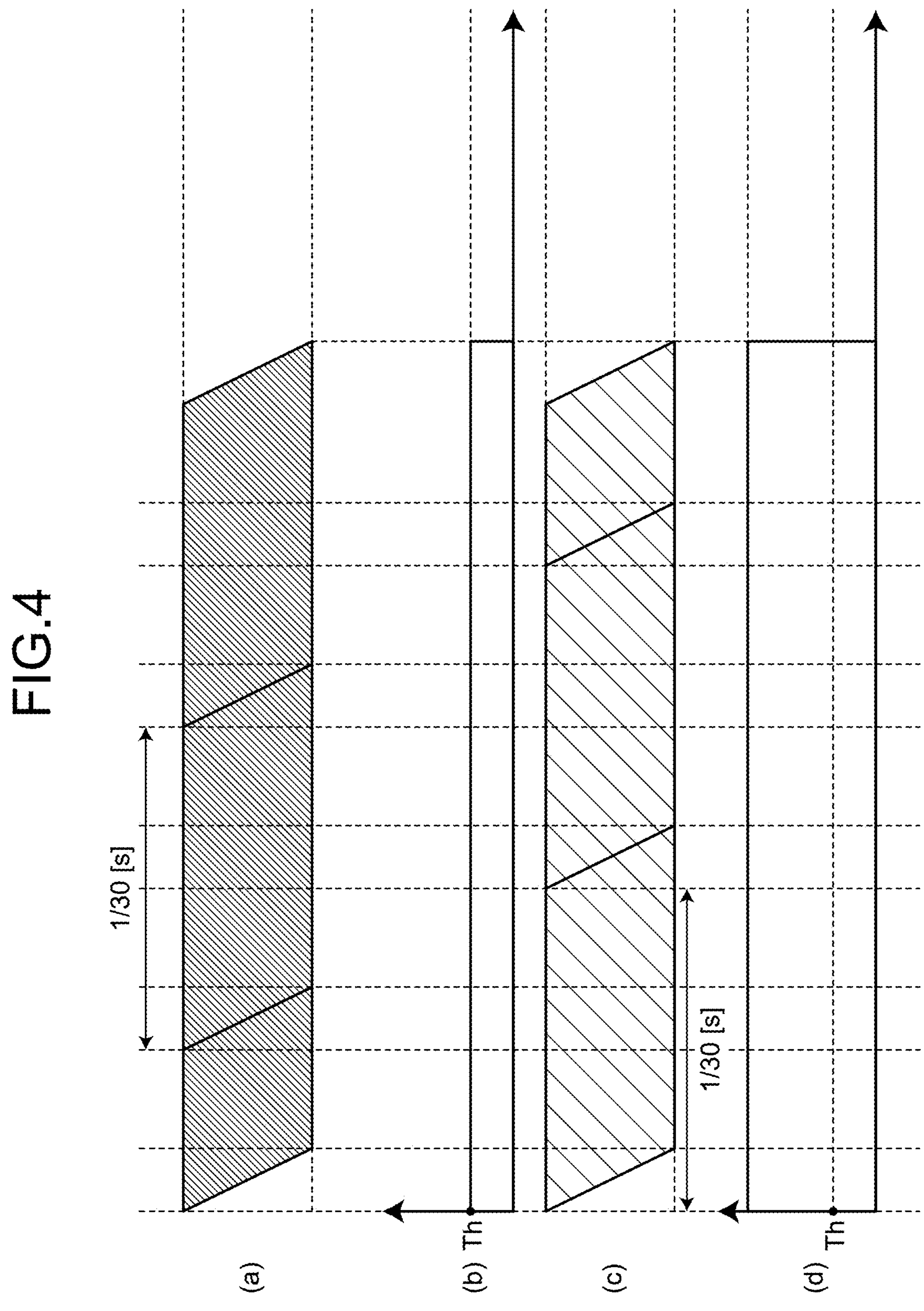
FIG. 4 is a diagram for describing the functions of the dimming control unit and the imaging control unit.
Figure 5:
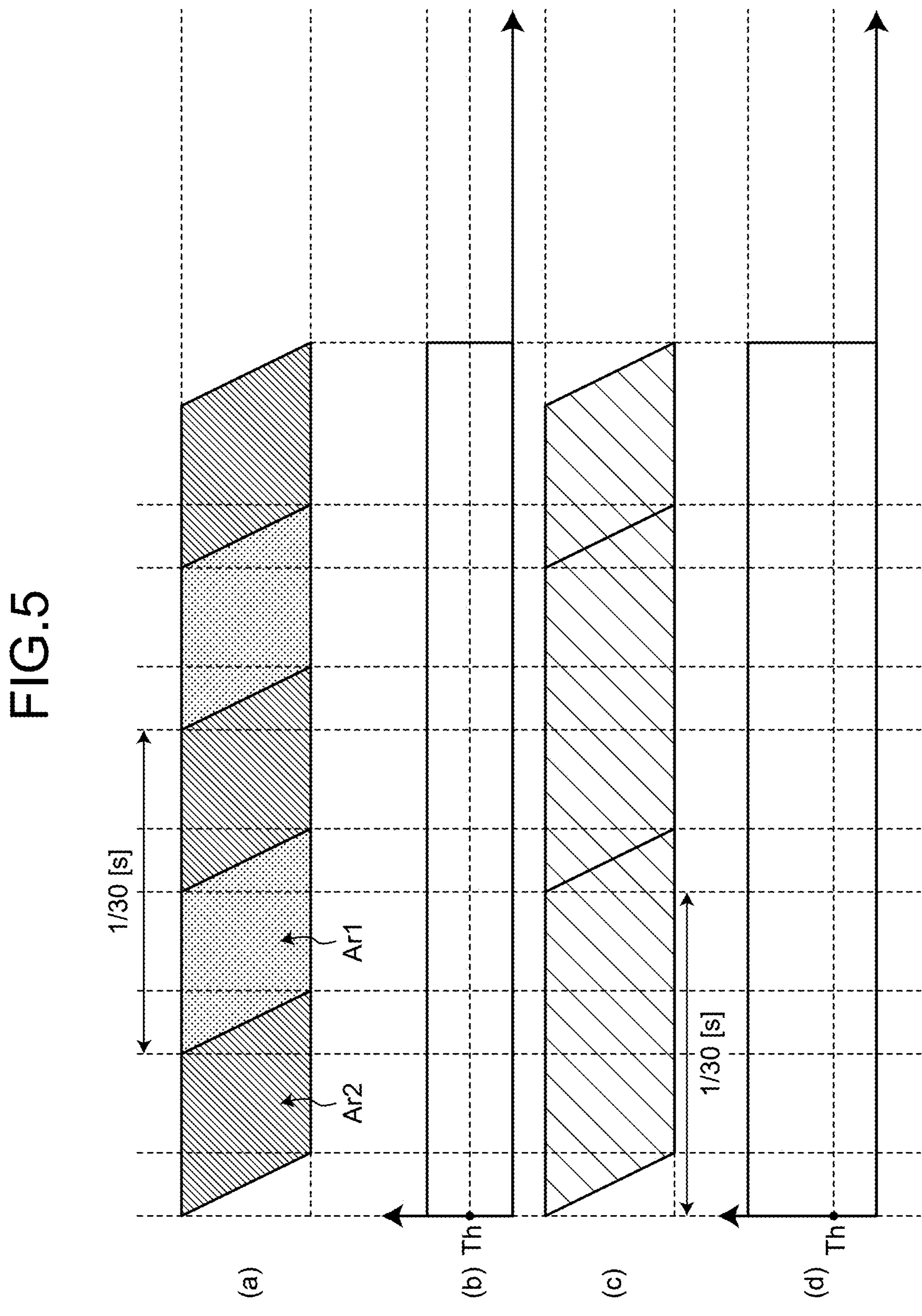
FIG. 5 is a diagram for describing the functions of the dimming control unit and the imaging control unit.

FIGS. 3 to 5 are diagrams for describing the functions of the dimming control unit 942 and the imaging control unit 943. Specifically, FIGS. 3 and 4 are diagrams for describing problems of dimming control and imaging control. FIG. 5 is a diagram for describing the second processing. Here, (a) of FIG. 3, (a) of FIG. 4, and (a) of FIG. 5 are diagrams illustrating imaging control of the second imaging element 532, where a vertical axis represents a horizontal line of the second imaging element 532 (an uppermost line indicates an uppermost horizontal line (first horizontal line) and a lowermost line indicates a lowermost horizontal line (last line)), and a horizontal axis represents time. Then, a parallelogram region is a region that contributes to generation of the normal light image in one field. (b) of FIG. 3, (b) of FIG. 4, and (b) of FIG. 5 are diagrams illustrating the dimming control, where a vertical axis represents a power value [W] to be supplied to the second light source 32, and a horizontal axis represents time (supply time of power to be supplied to the second light source 32). In the present embodiment, since a voltage value supplied to the second light source 32 is fixed, the vertical axis corresponds to a current value supplied to the second light source 32 in (b) of FIG. 3, (b) of FIG. 4, and (b) of FIG. 5. (c) of FIG. 3, (c) of FIG. 4, and (c) of FIG. 5 are diagrams illustrating imaging control of the first imaging element 531, where a vertical axis represents a horizontal line of the first imaging element 531 (an uppermost line indicates an uppermost horizontal line (first horizontal line), and a lowermost line indicates a lowermost horizontal line (last line)), and a horizontal axis represents time. A parallelogram region is a region that contributes to generation of the fluorescence image in one field. (d) of FIG. 3, (d) of FIG. 4, and (d) of FIG. 5 are diagrams illustrating the dimming control, where a vertical axis represents a power value [W] to be supplied to the first light source 31, and a horizontal axis represents time (supply time of power to be supplied to the first light source 31). In the present embodiment, since the voltage value supplied to first light source 31 is fixed, the vertical axis corresponds to the current value supplied to first light source 31 in (d) of FIG. 3, (d) of FIG. 4, and (d) of FIG. 5.

Hereinafter, problems of the dimming control and imaging control and second processing for solving the problems will be sequentially described.

Problems of Dimming Control and Imaging Control

First, problems of the dimming control and imaging control will be described with reference to FIGS. 3 and 4.

The imaging control unit 943 sequentially starts exposure of the first and second imaging elements 531 and 532 in one field period for each horizontal line, and performs so-called rolling shutter type imaging control of sequentially performing reading for each horizontal line for which a predetermined period (so-called shutter speed) has elapsed from the start of exposure. Then, in the imaging control, in the case of the NTSC system, it is conceivable to set one field to 1/60 [s] ((a) of FIG. 3 and (c) of FIG. 3).

Meanwhile, in the fluorescence image, the fluorescence from the observation target is minute, and the signal level is very low. Then, in order to increase the signal level, it is conceivable to perform long-time exposure in which a plurality of fields is set as one field in a pseudo manner ((a) of FIG. 4 and (c) of FIG. 4). The examples in (a) of FIG. 4 and (c) of FIG. 4 are examples in which two fields are set as one field in a pseudo manner, and the one field is set to 1/30 [s].

Note that, in the present embodiment, in a case where the medical observation system 1 is in the normal observation mode, the imaging control unit 943 sets one field to 1/60 [s] and executes imaging control of only the second imaging element 532. Meanwhile, in a case where the medical observation system 1 is in the fluorescence observation mode, the imaging control unit 943 sets one field to 1/30 [s] and executes long-time exposure (imaging control) of the first and second imaging elements 531 and 532. That is, the imaging control unit 943 executes first processing (long-time exposure) for changing the exposure periods of the first and second imaging elements 531 and 532. Note that, here, by exposing not only the first imaging element that captures the fluorescence but also the second imaging element that captures the normal light image for a long time, the amount of image data per unit time including the captured fluorescence image and the normal light image can be reduced. Therefore, even in a case where there is a restriction on the amount of image data per unit time that can be transmitted from the imaging unit, imaging can be performed within the restriction.

When the medical observation system 1 is in the normal observation mode, the dimming control unit 942 executes a normal dimming control described below.

That is, the dimming control unit 942 adjusts the normal light image to the reference brightness based on the brightness (average value of luminance values, or the like) of a specific region (detection region) in the normal light image. More specifically, the dimming control unit 942 adjusts a current value to be supplied to the second light source 32.

In addition, in a case where the medical observation system 1 is in the fluorescence observation mode, the dimming control unit 942 executes a dimming control for maintaining the light amount ratio illustrated below.

That is, the dimming control unit 942 executes the normal dimming control described above to adjust the brightness of the normal light image, and refers to the ratio information indicating the light amount ratio stored in the storage unit 97 to adjust the current value to be supplied to the first light source 31 in accordance with the adjustment of the current value to be supplied to the second light source 32 so as to maintain a state in which the ratio between the light amount of the white light emitted from the second light source 32 and the light amount of the near-infrared excitation light emitted from the first light source 31 is a specific ratio, thereby adjusting the brightness of the fluorescence image.

However, in a case where the above-described first processing (long-time exposure) and the above-described dimming control for maintaining the light amount ratio are used in combination, the following problems may occur.

That is, in a case where the first processing (long-time exposure) is executed, not only the signal level in the fluorescence image but also the signal level in the normal light image increases (about twice in the example of FIG. 4). That is, since the brightness of the normal light image becomes high, when the dimming control for maintaining the light amount ratio is executed, the light amount of the white light is decreased to adjust the brightness of the normal light image to the reference brightness, and the light amount of the near-infrared excitation light is also decreased in accordance with the decrease in the light amount of the white light. Therefore, as a result, there is a first problem that the brightness of the fluorescence image decreases.

Therefore, in order to solve the first problem, the following method is considered.

As illustrated in (b) of FIG. 4, while the power of N [W] is originally supposed to be supplied to the second light source 32, power of N/2 [W] which is half the power is supplied to second light source 32. In this way, the normal light image does not become brighter than necessary, and the brightness of the fluorescence image does not decrease even when the dimming control for maintaining the light amount ratio is executed. However, this method has the following second problem.

Since the light amount of the white light emitted from the second light source 32 is greatly reduced, the margin of the current value for adjusting the light amount of the white light emitted from the second light source 32 is reduced. Furthermore, in the dimming control for maintaining the light amount ratio, since the light amount of the near-infrared excitation light is adjusted in accordance with the light amount of the white light, the margin of the current value for adjusting the light amount of the near-infrared excitation light emitted from the first light source 31 is also reduced.

Then, in the present embodiment, the imaging control unit 943 executes the following second processing to solve the second problem.

Second Processing

Next, the second processing executed by the imaging control unit 943 will be described with reference to FIG. 5.

The second processing is processing of discarding image information generated by the second imaging element 532 according to light reception in a part of the exposure period of the second imaging element 532. In the present embodiment, the second processing is processing of adjusting a diaphragm amount of the electronic shutter of the second imaging element 532. That is, in the present embodiment, the image information corresponds to a charge accumulated for each pixel by the second imaging element 532. In the example of FIG. 5, the imaging control unit 943 fixes the diaphragm amount of the electronic shutter of the second imaging element 532 to 1/60 [s]. Note that, in (a) of FIG. 5, a region Ar1 indicated by a dot is a region indicating sweeping of charges by the electronic shutter. Furthermore, a hatched region Ar2 is a region indicating an effective exposure period.

According to the present embodiment described above, the following effects are obtained.

In the control device 9 according to the present embodiment, the imaging control unit 943 executes the first processing and second processing described above.

Therefore, according to the control device 9 of the present embodiment, the above-described first and second problems can be solved, and dimming control of the light source device 3 can be appropriately performed.

Other Embodiments

Although the embodiments for carrying out the present disclosure have been described so far, the present disclosure should not be limited only by the above-described embodiments.

A configuration of first to eleventh modifications described below may be adopted.

First Modification

Figure 7:
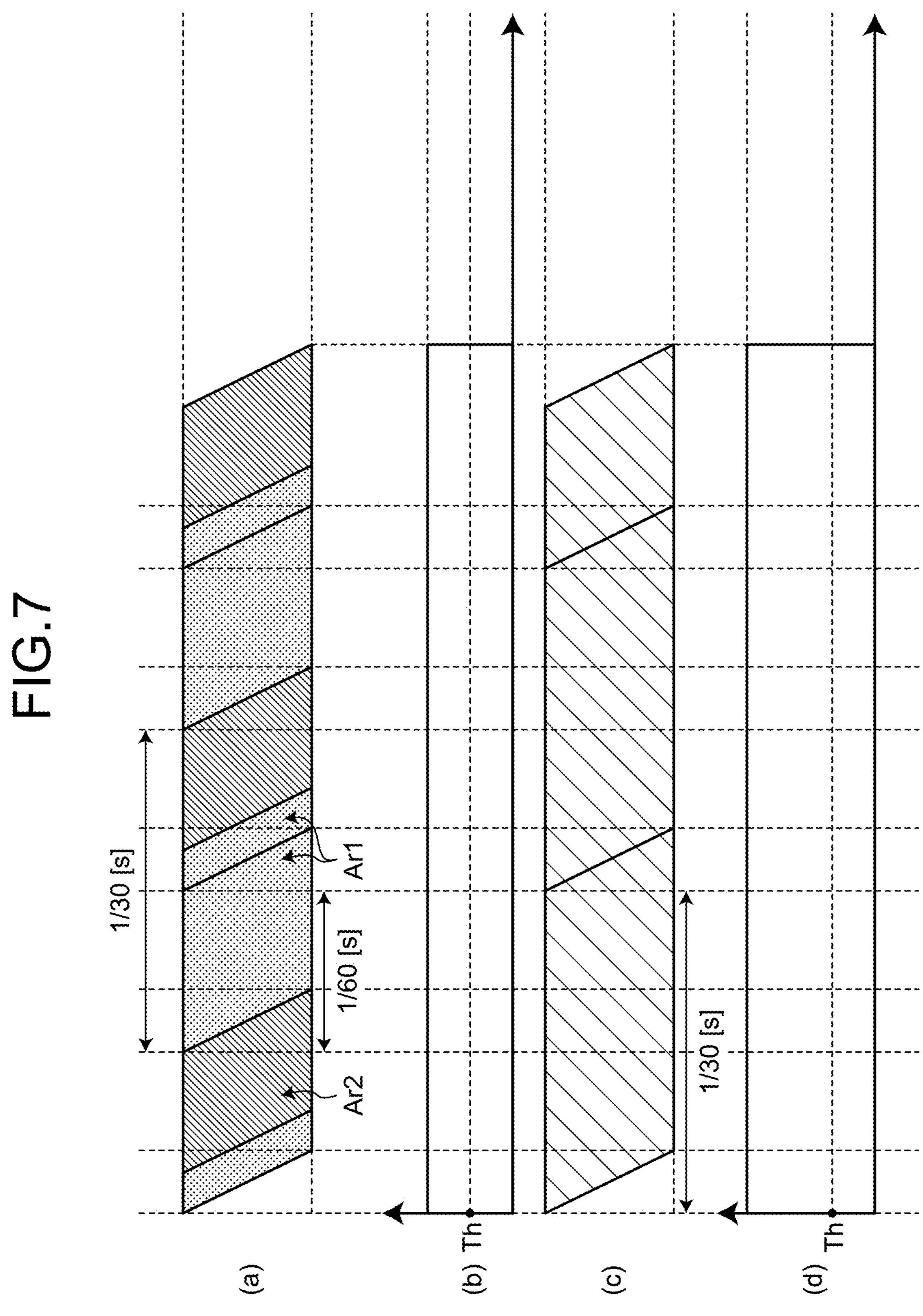
FIG. 7 is a diagram illustrating the first modification of the embodiment.

FIGS. 6 and 7 are diagrams illustrating a first modification of the embodiment. Specifically, FIG. 6 is a diagram corresponding to FIG. 2. FIG. 7 is a diagram corresponding to FIG. 5. Note that (d) of FIG. 7 is a diagram illustrating a dimming control, where a vertical axis represents a power value [W] to be supplied to a third light source 33, and a horizontal axis represents time (supply time of power to be supplied to the third light source 33).

In the above-described embodiment, as the first light according to the present disclosure, the near-infrared excitation light used in a technology called Infra-Red Imaging (IRI) which is special light observation is adopted, but the present disclosure is not limited thereto, and special light used in other special light observation (technology called Narrow Band Imaging (NBI), technology called Auto Fluorescence Imaging (AFI), technology called Photodynamic Diagnosis (PDD), and the like) may be adopted. In addition, a plurality of special light may be employed as the first light according to the present disclosure.

In the first modification, two types of light, that is, near-infrared excitation light and special light (hereinafter, described as second special light) different from the near-infrared excitation light are adopted as the first light according to the present disclosure. That is, as illustrated in FIG. 6, in a light source device 3A according to the first modification, the third light source 33 that emits the second special light is added to the light source device 3 described in the above-described embodiment.

In the first modification, as the mode of the medical observation system 1, a second special light observation mode is provided in addition to the normal observation mode and the fluorescence observation mode.

The second special light observation mode is a mode in which the second special light image and the normal light image are generated, and the second special light image and the normal light image (or superimposed image obtained by superimposing the second special light image and the normal light image) are displayed on the display device 7. Note that the second special light image is a captured image in which the observation target is irradiated with the second special light, and the second imaging element 532 captures return light of the second special light via the observation target.

In the second special light observation mode, the control unit 94 simultaneously turns on the second and third light sources 32 and 33. Furthermore, the communication unit 54 alternately transmits the second special light image and the normal light image generated by the imaging unit 53 to the communication unit 91. Furthermore, the processing module 93 executes image processing on each of the second special light image and the normal light image received by the communication unit 91, generates a video signal for displaying the second special light image and the normal light image (or superimposed image obtained by superimposing the second special light image and the normal light image) after execution of the image processing, and outputs the video signal to the display device 7. As a result, the second special light image and the normal light image (or superimposed image obtained by superimposing the second special light image and the normal light image) are displayed on the display device 7.

Furthermore, in the first modification, when executing the second processing in the second special light observation mode, as illustrated in (a) of FIG. 7, the imaging control unit 943 sets the diaphragm amount of the electronic shutter of the second imaging element 532 to a diaphragm amount different from the second processing in the fluorescence observation mode. In the example of FIG. 7, the imaging control unit 943 sets the diaphragm amount of the electronic shutter of the second imaging element 532 to a diaphragm amount larger than 1/60 [s]. That is, in the second processing, the imaging control unit 943 sets the diaphragm amount of the electronic shutter of the second imaging element 532 to the diaphragm amount corresponding to the first light emitted from the light source device 3 among the plurality of first light.

According to the first modification described above, even in a case where the first light is changed, the same effects as those of the above-described embodiment are obtained.

Second Modification

Figure 8:
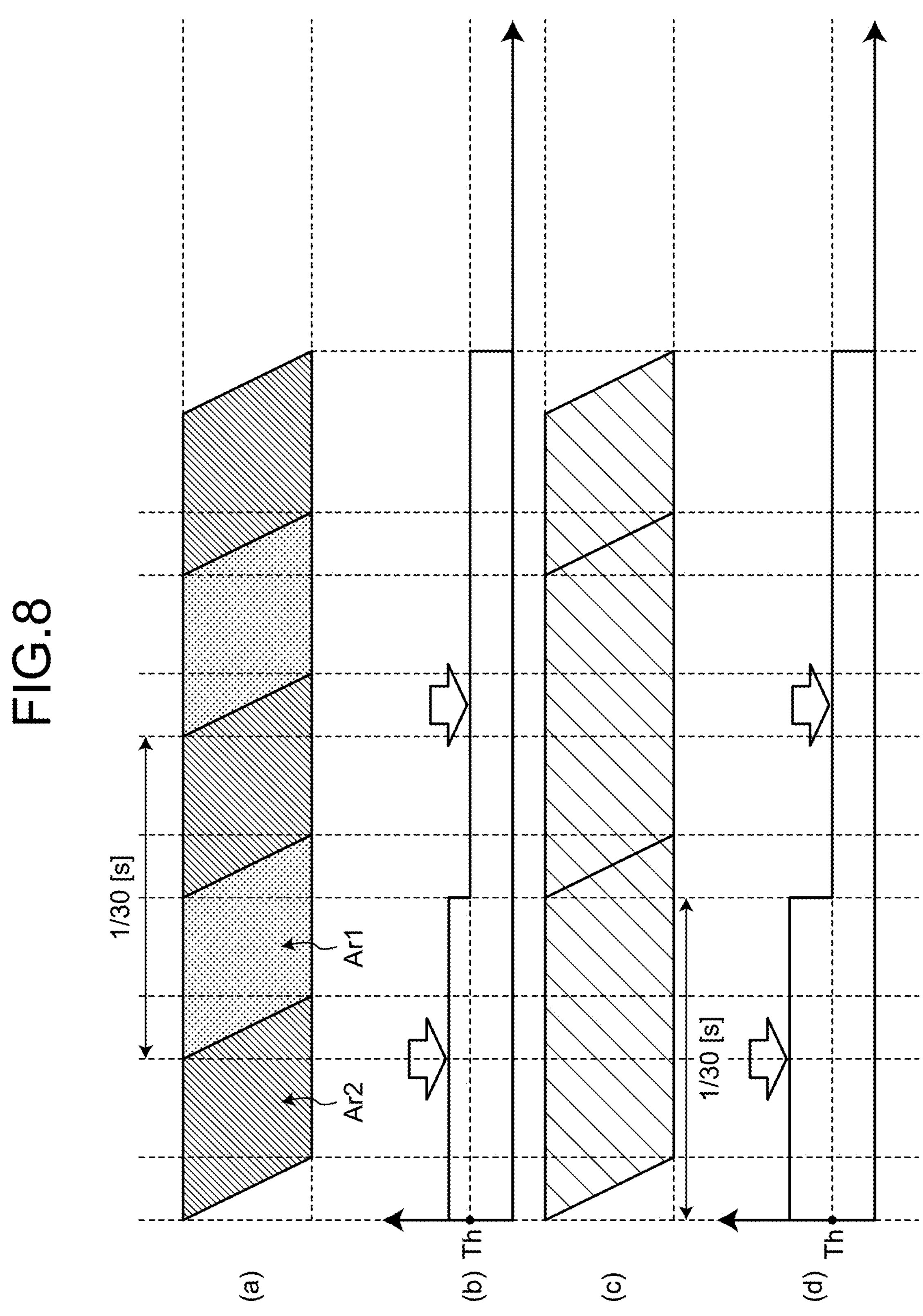
FIG. 8 is a diagram illustrating a second modification of the embodiment.
Figure 9:
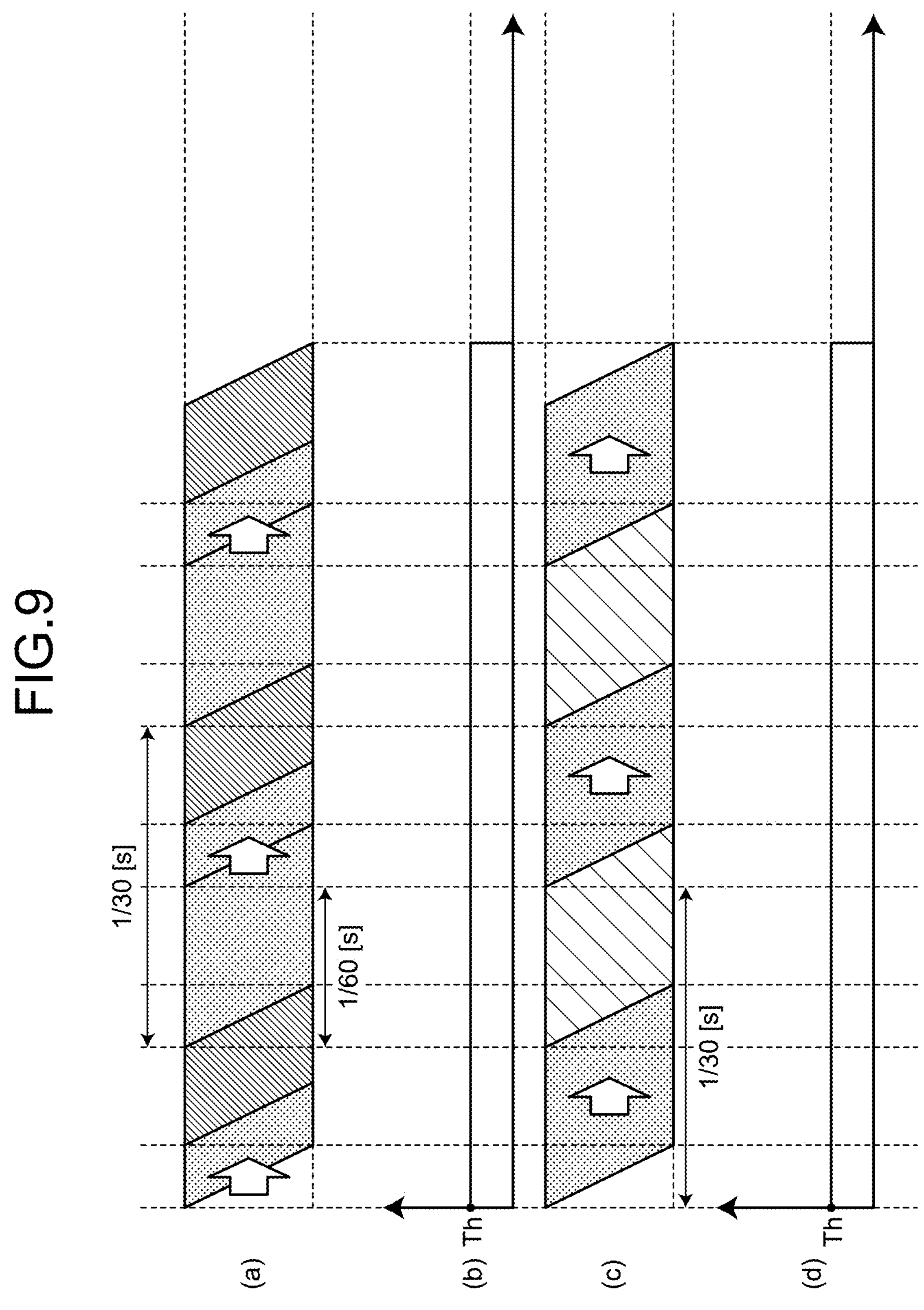
FIG. 9 is a diagram for describing the second modification of the embodiment.

FIGS. 8 and 9 are diagrams for describing a second modification of the embodiment. Specifically, FIGS. 8 and 9 are diagrams corresponding to FIG. 5.

In the above-described embodiment, in a case where the medical observation system 1 is in the fluorescence observation mode, when the brightness of the fluorescence image and the normal light image is lowered, dimming control and imaging control may be executed as in the second modification illustrated in FIGS. 8 and 9.

Specifically, as illustrated in FIG. 8, the dimming control unit 942 decreases the current value supplied to the first and second light sources 31 and 32 (decreases the light amounts of the near-infrared excitation light and the white light) while performing the dimming control to maintain the light amount ratio.

Then, as illustrated in FIG. 8, after the current values supplied to the first and second light sources 31 and 32 decrease to the drive limit value Th, the imaging control unit 943 increases the diaphragm amount of the electronic shutter of the first imaging element 531 and the diaphragm amount of the electronic shutter of the second imaging element 532 while maintaining a state in which the ratio between the effective exposure period (period indicated by region Ar1) of the first imaging element 531 and the effective exposure period of the second imaging element 532 (period indicated by region Ar2) is a specific ratio. In the examples of FIGS.

8 and 9, in the initial state (state before the current value reaches the drive limit value Th), the effective exposure period of the first imaging element 531 is 1/30 [s], and the effective exposure period of the second imaging element 532 is 1/60 [s]. Therefore, the imaging control unit 943 sequentially increases the diaphragm amount of the electronic shutter of the first imaging element 531 and the diaphragm amount of the electronic shutter of the second imaging element 532 in the form of the effective exposure period of the first imaging element 531: 1/60 [s], the effective exposure period of the second imaging element 532: 1/120 [s] (state of FIG. 9), the effective exposure period of the first imaging element 531: 1/120 [s], and the effective exposure period of the second imaging element 532: 1/240 [s], . . . while maintaining the ratio of the respective effective exposure periods.

Even in a case where the configuration of the second modification described above is adopted, the same effects as those of the above-described embodiment are obtained.

Third Modification

Figure 11:
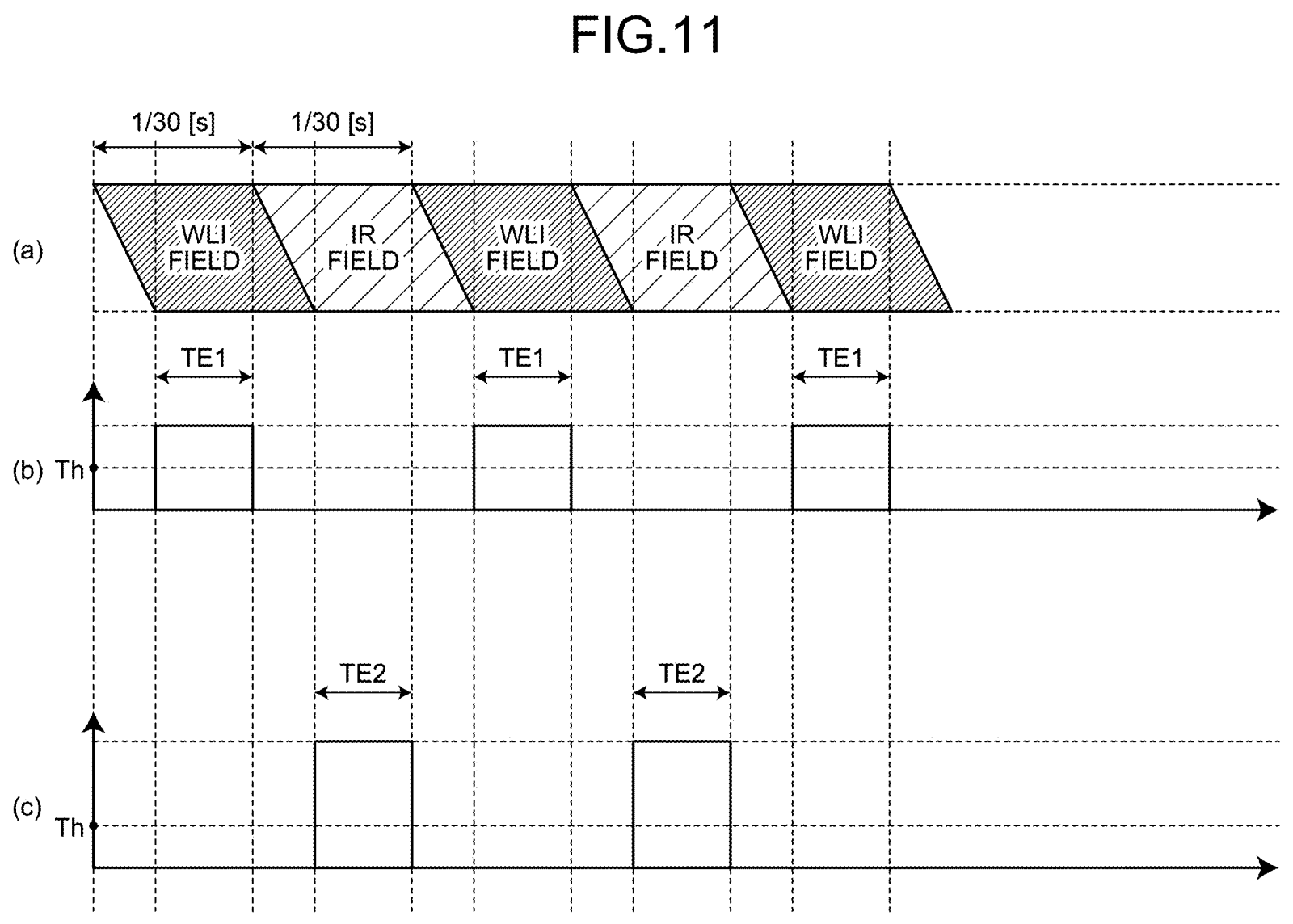
Figure 12:
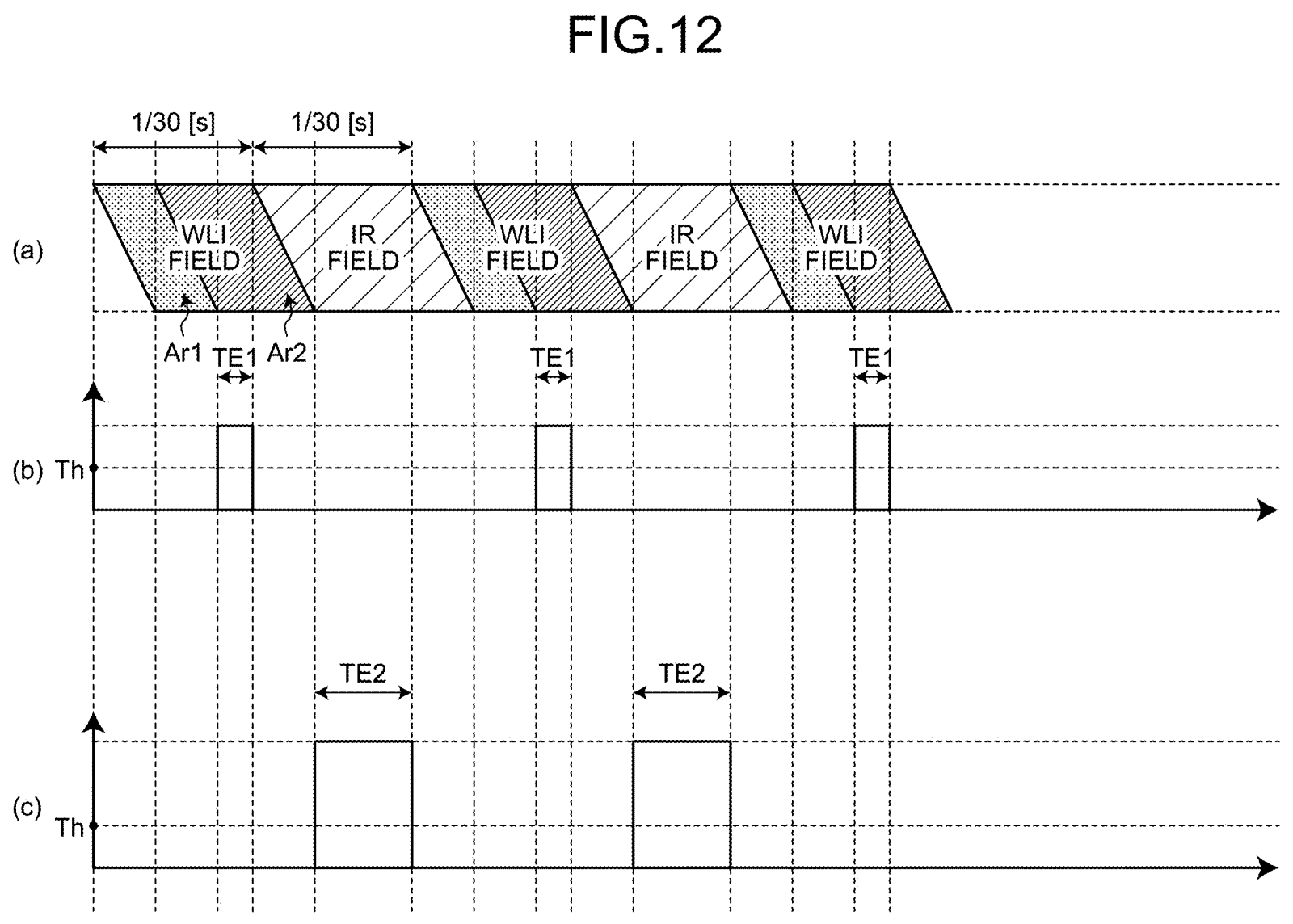

FIGS. 10 to 12 are diagrams for describing a third modification of the embodiment. Specifically, FIG. 10 is a diagram corresponding to FIG. 2. FIGS. 11 and 12 are diagrams for describing the functions of the dimming control unit 942 and the imaging control unit 943 according to the third modification. Here, (a) of FIG. 11 and (a) of FIG. 12 are diagrams illustrating imaging control of the first imaging element 531, where a vertical axis represents the horizontal line of the first imaging element 531 (an uppermost line indicates an uppermost horizontal line (first horizontal line), and a lowermost line indicates a lowermost horizontal line (last line)), and a horizontal axis represents time. A parallelogram region is a region that contributes to the generation of the normal light image and the fluorescence image in one field. Note that, in FIGS. 11 and 12, a parallelogram region contributing to generation of the normal light image is described as a white light imaging (WLI) field, and a parallelogram region contributing to generation of a fluorescence image is described as an infra-red (IR) field. (b) of FIG. 11 and (b) of FIG. 12 are diagrams illustrating dimming control, where a vertical axis represents a power value [W] to be supplied to the second light source 32, and a horizontal axis represents time (supply time of power to be supplied to second light source 32). Note that, in the third modification, similarly to the above-described embodiment, since a voltage value supplied to the second light source 32 is fixed, a vertical axis corresponds to a current value supplied to the second light source 32 in (b) of FIG. 11 and (b) of FIG. 12. (c) of FIG. 11 and (c) of FIG. 12 are diagrams illustrating dimming control, where a vertical axis represents the power value [W] to be supplied to the first light source 31, and a horizontal axis represents time (supply time of power to be supplied to the first light source 31). Note that, in the third modification, similarly to the above-described embodiment, since the voltage value supplied to the first light source 31 is fixed, the vertical axis corresponds to the current value supplied to the first light source 31 in (c) of FIG. 11 and (c) of FIG. 12.

In the above-described embodiment, the imaging unit 53 includes two imaging elements of the first and second imaging elements 531 and 532, but is not limited thereto, and may include only one imaging element. For example, as illustrated in FIG. 10, an imaging unit 53B according to the third modification does not include the prism 52 and includes only one first imaging element 531 as compared with the imaging unit 53 described in the above-described embodiment.

Then, in the fluorescence observation mode according to the third modification, the dimming control unit 942 and the imaging control unit 943 execute the following processing.

Similarly to the above-described embodiment, the imaging control unit 943 performs long-time exposure (first processing). In the examples of FIGS. 11 and 12, the imaging control unit 943 sets one field collected in a pseudo manner to 1/30 [s]. Note that, in a case where the medical observation system 1 is in the normal observation mode, the imaging control unit 943 sets one field to 1/60 [s] as in the above-described embodiment.

As illustrated in FIG. 11, the dimming control unit 942 alternately repeats the light emission of the first light source 31 and the light emission of the second light source 32 for each of the fields collected in a pseudo manner. Specifically, the dimming control unit 942 causes the second light source 32 to emit light in the full line exposure period TE1 ((b) of FIG. 11) in the WLI field of the alternately repeated WLI field and IR field. Meanwhile, the dimming control unit 942 causes the first light source 31 to emit light in the full line exposure period TE2 ((c) of FIG. 11) in the IR field of the alternately repeated WLI field and IR field. Here, the full line exposure periods TE1 and TE2 are periods in which all the horizontal lines in the effective pixel region in the first imaging element 531 are simultaneously exposed.

In addition, the dimming control unit 942 executes the normal dimming control and the dimming control for maintaining the light amount ratio, similarly to the above-described embodiment.

Here, in a case where the dimming control unit 942 and the imaging control unit 943 perform the above-described dimming control and imaging control (FIG. 11), the first and second problems described in the above-described embodiment may occur.

Therefore, also in the third modification, the imaging control unit 943 executes the second processing as illustrated in (a) of FIG. 12. Specifically, the imaging control unit 943 fixes the diaphragm amount of the electronic shutter of the first imaging element 531 to a predetermined value in the WLI field. Note that, in (a) of FIG. 12, a region Ar1 indicated by a dot is a region indicating sweeping of charges by the electronic shutter. Furthermore, a hatched region Ar2 is a region indicating an effective exposure period.

Furthermore, in the WLI field, as a result of narrowing by the electronic shutter, the full line exposure period TE1 is shortened as illustrated in (b) of FIG. 12. Then, the dimming control unit 942 causes the second light source 32 to emit light over the shortened full line exposure period TE1.

Even in a case where the configuration of the third modification described above is adopted, the same effects as those of the above-described embodiment are obtained.

Fourth Modification

Figure 13:
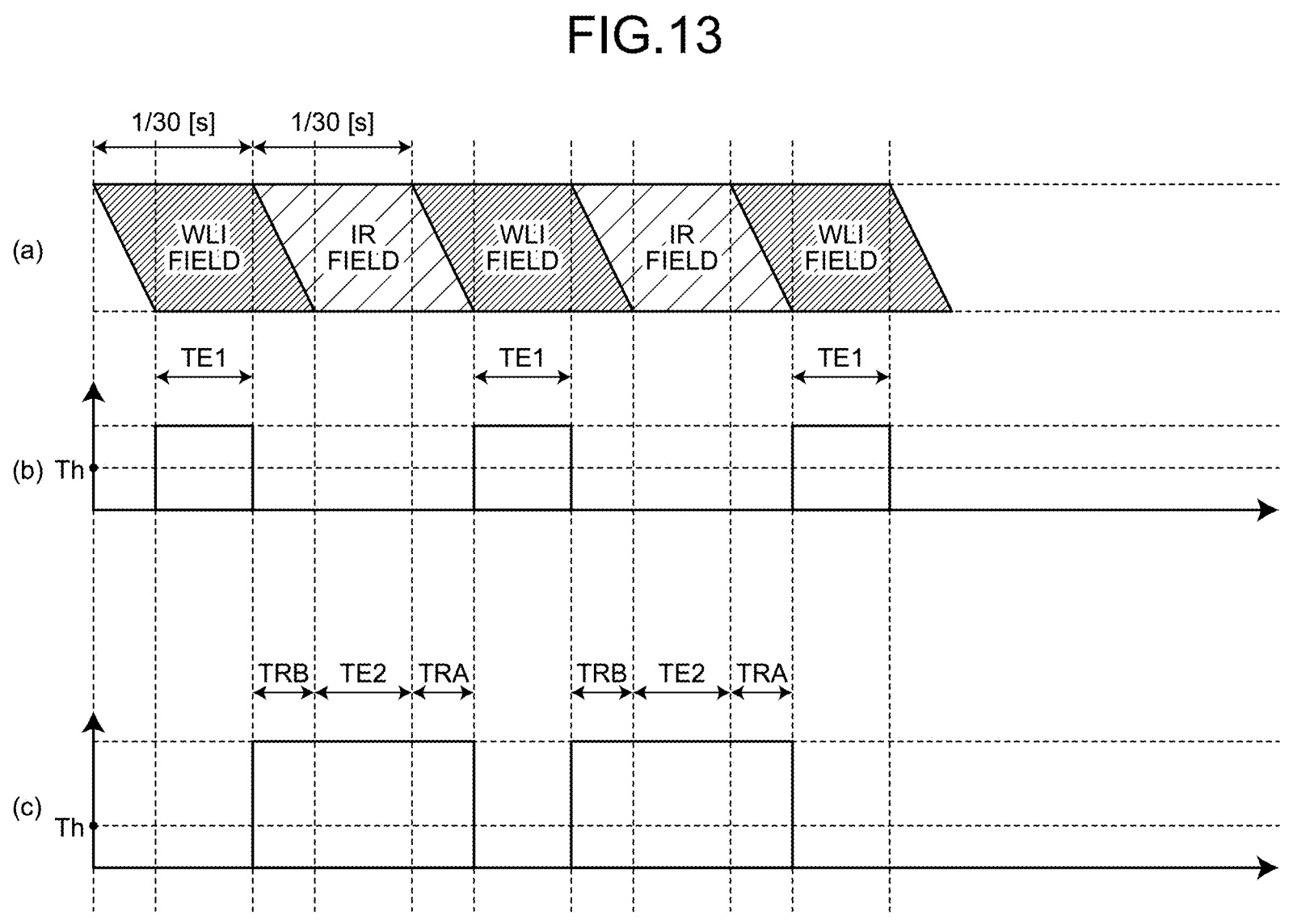
Figure 14:
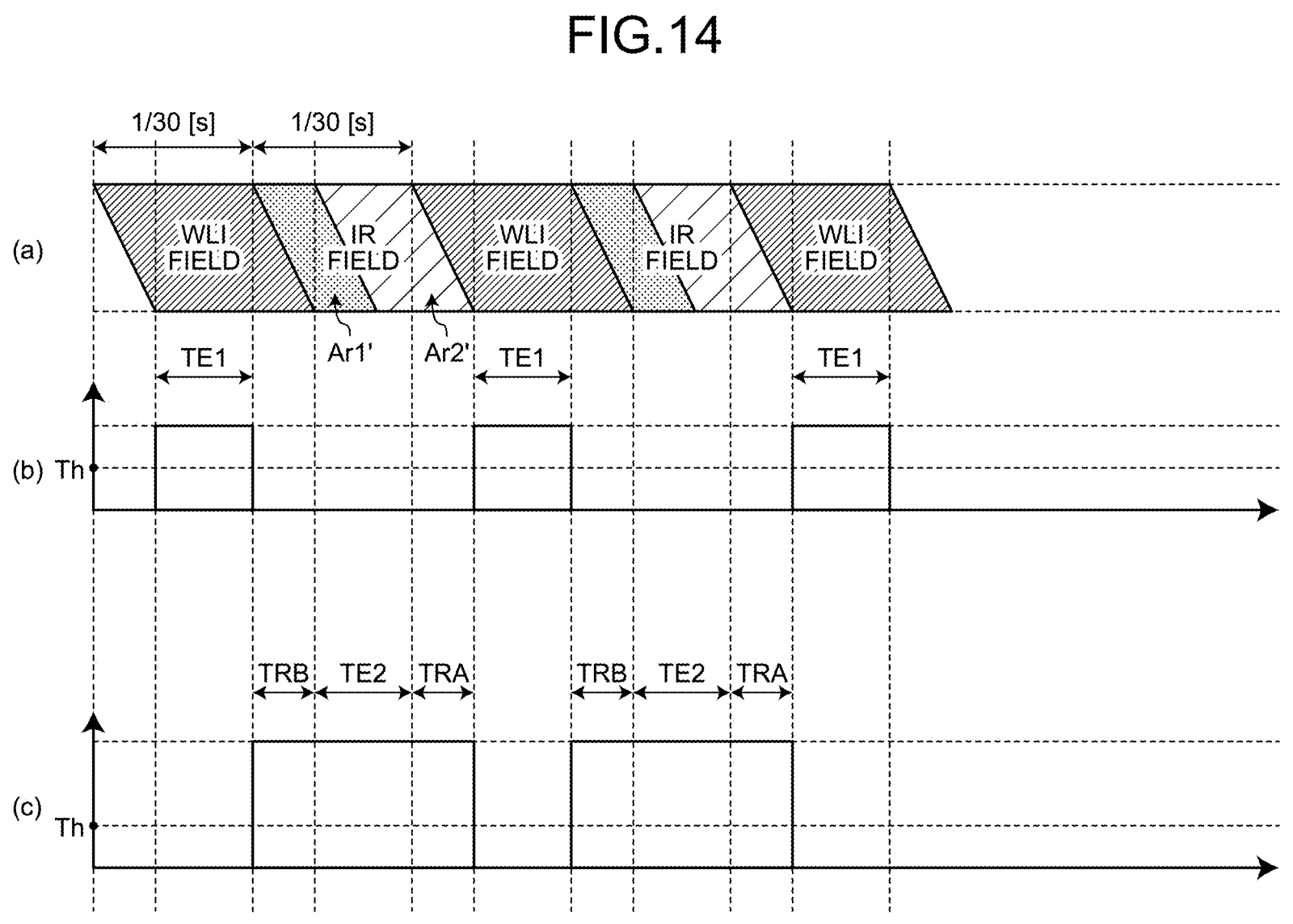

FIGS. 13 and 14 are diagrams for describing a fourth modification of the embodiment. Specifically, FIGS. 13 and 14 are diagrams corresponding to FIGS. 11 and 12.

In the above-described third modification, when the medical observation system 1 is in the fluorescence observation mode, the dimming control unit 942 causes the first light source 31 to emit light over the full line exposure period TE2 in the IR field of the alternately repeated WLI field and IR field, but the present disclosure is not limited thereto.

As illustrated in FIGS. 13 and 14, the dimming control unit 942 according to the fourth modification causes the first light source 31 to emit light in a period including the full line exposure period TE2 in the IR field, at least a part of a read period TRB, and at least a part of a read period TRA of the WLI field and the IR field that are alternately repeated.

Here, the read period TRB is a read period for reading the charges accumulated in the plurality of pixels of the first imaging element 531, is adjacent to the full line exposure period TE2, and is a read period before the full line exposure period TE2 in time series. Furthermore, the read period TRA is a read period for reading the charges accumulated in the plurality of pixels of the first imaging element 531, is adjacent to the full line exposure period TE2, and is a read period after the full line exposure period TE2 in time series.

Furthermore, in the above-described third modification, in a case where the medical observation system 1 is in the fluorescence observation mode, the imaging control unit 943 fixes the diaphragm amount of the electronic shutter of the first imaging element 531 to the predetermined value in the WLI field, but the present disclosure is not limited thereto.

As illustrated in FIG. 14, the imaging control unit 943 according to the fourth modification fixes the diaphragm amount of the electronic shutter of the first imaging element 531 to a predetermined value in the IR field. Note that, in FIG. 14 (a), a region Ar1' indicated by a dot is a region indicating the sweeping of the charge by the electronic shutter. Furthermore, a hatched region Ar2' is a region indicating an effective exposure period.

Even in a case where the configuration of the fourth modification described above is adopted, the same effects as those of the above-described embodiment and third modification are obtained.

Fifth Modification

Figure 15:
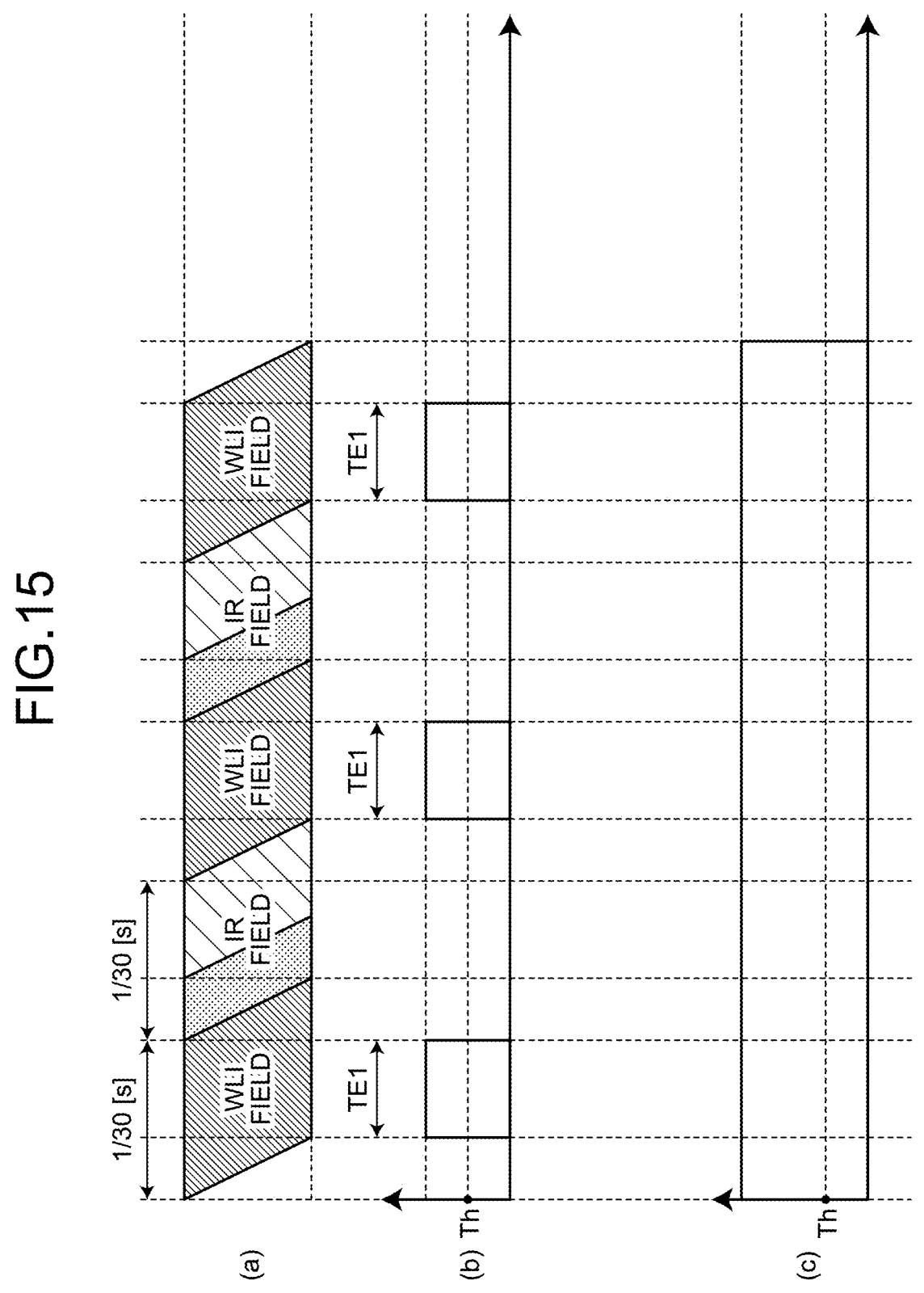

FIG. 15 is a diagram for describing a fifth modification of the embodiment. Specifically, FIG. 15 is a diagram corresponding to FIG. 14.

In the above-described fourth modification, when the medical observation system 1 is in the fluorescence observation mode, the dimming control unit 942 may always turn on the first light source 31 as in the fifth modification illustrated in FIG. 15.

Even in a case where the configuration of the above-described fifth modification is adopted, the same effects as those of the above-described embodiment and the third and fourth modifications are obtained.

Sixth Modification

In the above-described embodiment, the first and second imaging elements 531 and 532 are configured by CMOS, but are not limited thereto, and may be configured by a charge coupled device (CCD).

Even in a case where the configuration of the above-described sixth modification is adopted, the same effects as those of the above-described embodiment are obtained.

Seventh Modification

In the above-described embodiment, as the second processing according to the present disclosure, the processing of adjusting the diaphragm amount of the electronic shutter of the second imaging element 532 is adopted, but the present disclosure is not limited thereto.

In a case where the medical observation system 1 is in the fluorescence observation mode, the imaging control unit 943 according to the seventh modification performs long-time exposure only for the first imaging element 531, and sets one field to 1/60 [s] for the second imaging element 532 as in the case of the normal observation mode. Then, the imaging control unit 943 may be configured to control the operation of the communication unit 54 so as not to transmit the normal light image of one field to the communication unit 91 once for two fields among the normal light images generated by the second imaging element 532. The normal light image of one field that is not transmitted corresponds to image information according to the present disclosure.

Even in a case where the configuration of the above-described seventh modification is adopted, the same effects as those of the above-described embodiment are obtained.

Eighth Modification

In the above-described embodiment, the read timing (hereinafter, it is described as first read timing.) for reading the charges accumulated in the plurality of pixels of the first imaging element 531 and the read timing (hereinafter, described as second read timing) for reading the charges accumulated in the plurality of pixels of the second imaging element 532 are shifted from each other, but the present disclosure is not limited thereto. A configuration in which the first and second read timings are the same may be adopted.

Even in a case where the configuration of the eighth modification described above is adopted, the same effects as those of the above-described embodiment are obtained.

Ninth Modification

In the above-described embodiment, the case of the NTSC system is exemplified, and 1/60 [s] is used as a reference, but the present disclosure is not limited thereto. In the case of the PAL method, 1/50 [s] may be used as a reference, or high-speed imaging operation (for example, 1/240 [s]) may be used as a reference.

Even in a case where the configuration of the above-described ninth modification is adopted, the same effects as those of the above-described embodiment are obtained.

Tenth Modification

The medical observation system according to the tenth modification is a medical observation system using a so-called video scope (flexible endoscope) having an imaging unit on the distal end side of the insertion unit. Hereinafter, for convenience of description, the medical observation system 1 according to the tenth modification will be referred to as a medical observation system 1C.

Figure 16:
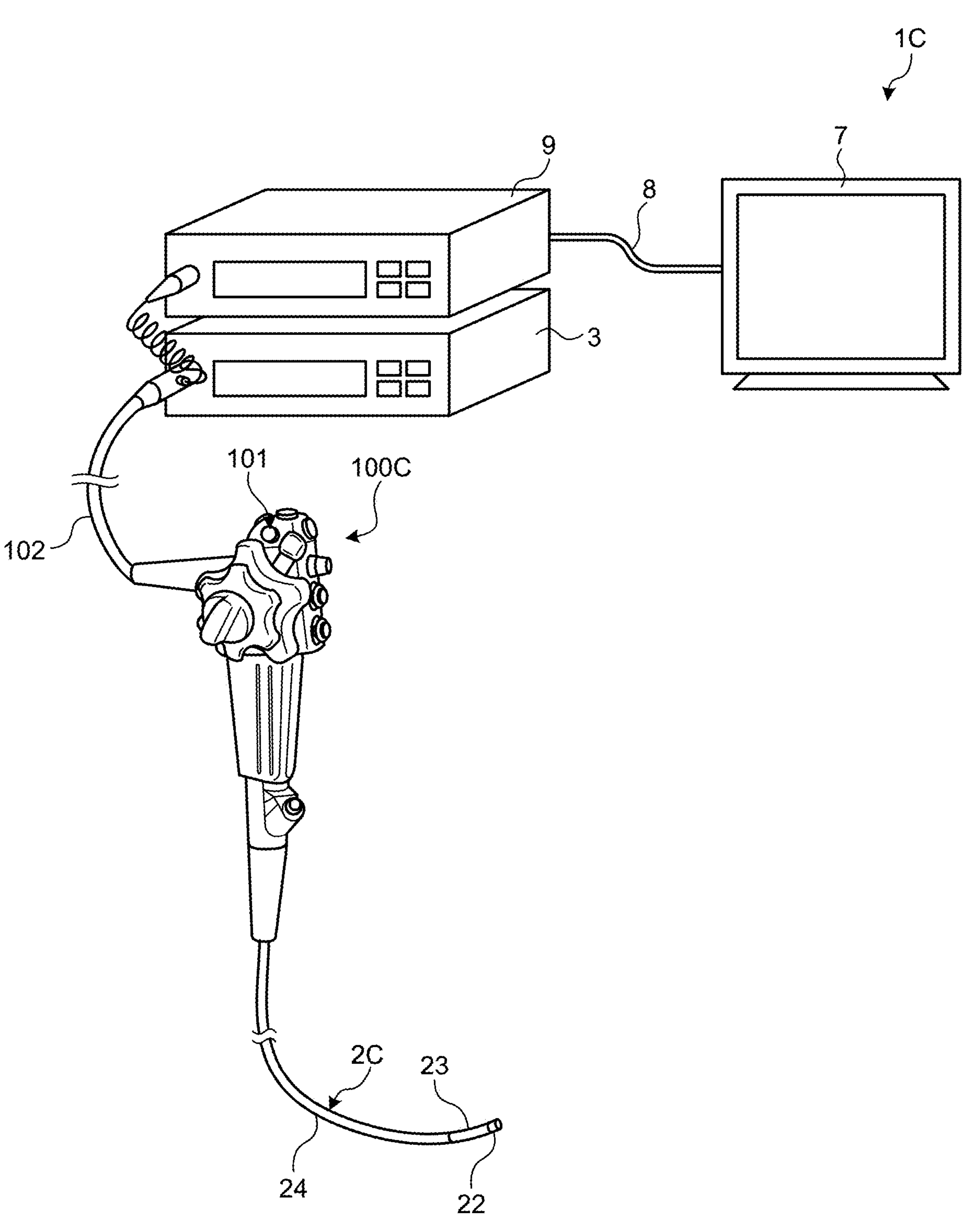
FIG. 16 is a diagram for describing an eleventh modification of the embodiment.

FIG. 16 is a diagram for describing the tenth modification of the embodiment.

As illustrated in FIG. 16, the medical observation system 1C includes an endoscope 100C that captures an in-vivo image of an observed region by inserting an insertion unit 2C into a living body and outputs a captured image, a light source device 3 that generates illumination light emitted from a distal end of the endoscope 100C, a control device 9 that processes the captured image output from the endoscope 100C, and a display device 7 that is connected to the control device 9 via a second transmission cable 8 and displays an image based on a video signal processed by the control device 9.

As illustrated in FIG. 16, the endoscope 100C includes an insertion unit 2C having a flexible elongated shape, an operating unit 101 connected to a proximal end side of the insertion unit 2C and receiving various operations, and a universal cord 102 extending in a direction different from a direction in which the insertion unit 2C extends from the operating unit 101 and incorporating various cables connected to the light source device 3 and the control device 9.

As illustrated in FIG. 16, the insertion unit 2C includes a distal end portion 22, a bendable bending unit 23 connected to the proximal end side of the distal end portion 22 and configured by a plurality of bending pieces, and an elongated flexible tube unit 24 connected to the proximal end side of the bending unit 23 and having flexibility.

Although not specifically illustrated, the distal end portion 22 incorporates substantially the same configuration as the camera head 5 described in the above-described embodiment. Then, the captured image captured by the distal end portion 22 (imaging unit) is output to the control device 9 via the operating unit 101 and the universal cord 102.

Even in a case where the configuration of the above-described tenth modification described above is adopted, the same effects as those of the above-described embodiment are obtained.

Eleventh Modification

A medical observation system according to an eleventh modification is a medical observation system using a surgical microscope that enlarges and captures a predetermined visual field area inside a subject (inside a living body) or on a surface of the subject (surface of the living body). Hereinafter, for convenience of description, the medical observation system 1 according to the eleventh modification will be referred to as a medical observation system 1D.

Figure 17:
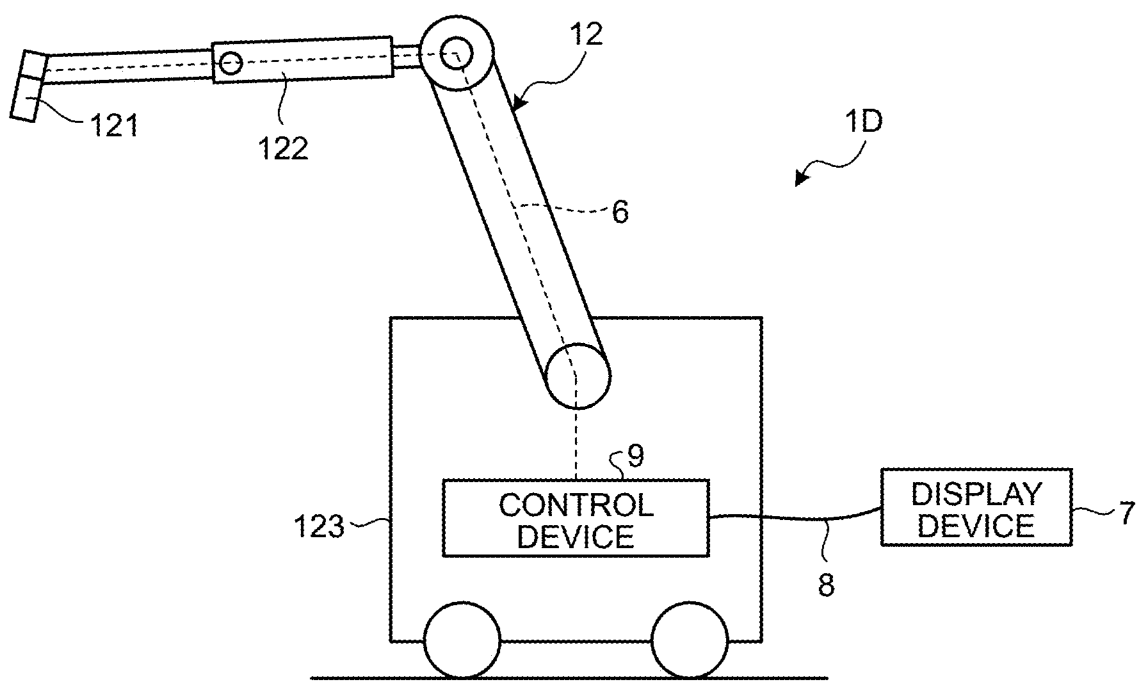
FIG. 17 is a diagram for describing the eleventh modification of the embodiment.

FIG. 17 is a diagram for describing the eleventh modification of the embodiment.

As illustrated in FIG. 17, the medical observation system 1D includes a surgical microscope 12 that captures an image for observing a subject and outputs a captured image, a control device 9 that processes the captured image output from the surgical microscope 12, and a display device 7 that is connected to the control device 9 via a second transmission cable 8 and displays an image based on a video signal processed by the control device 9.

As illustrated in FIG. 17, the surgical microscope 12 includes a microscope unit 121 that enlarges and captures a minute portion of a subject and outputs a captured image, a support unit 122 that is connected to a proximal end portion of the microscope unit 121 and includes an arm that rotatably supports the microscope unit 121, and a base unit 123 that rotatably holds the proximal end portion of the support unit 122 and is movable on a floor surface.

Then, as illustrated in FIG. 17, the control device 9 is installed on the base unit 123. Although not specifically illustrated, the base unit 123 is also provided with the light source device 3 that generates illumination light to be emitted from the surgical microscope 12 to the subject.

Note that the base unit 123 may be fixed to a ceiling, a wall surface, or the like to support the support unit 122, instead of being movably provided on the floor surface.

Although not specifically illustrated, the microscope unit 121 incorporates substantially the same configuration as the camera head 5 described in the above-described embodiment. Then, the captured image captured by the microscope unit 121 (imaging unit) is output to the control device 9 via the first transmission cable 6 wired along the support unit 122.

Even in a case where the configuration of the above-described eleventh modification is adopted, the same effects as those of the above-described embodiment are obtained.

Note that the following configurations also belong to the technical scope of the present disclosure.

According to the medical control device and the medical observation system according to the present disclosure, dimming control of the light source device can be appropriately performed.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical control device comprising:
circuitry configured to
control an operation of a light source configured to emit first light and second light having a wavelength band different from a wavelength band of the first light, and
adjust a light amount of the first light and a light amount of the second light,
control an operation of an imaging device including a first imaging element and a second imaging element,
irradiate an observation target with the first light to capture return light of the first light via the observation target to generate a first captured image, and
irradiate the observation target with the second light to capture return light of the second light via the observation target to generate a second captured image, wherein the circuitry is further configured to execute
first processing of changing an exposure period of the imaging element, and
second processing of discarding image information generated by the imaging element according to light reception in a partial period of the exposure period, and
the circuitry is further configured to control an increase, after the light amount of the first light and the light amount of the second light decrease to a drive limit value, a diaphragm amount of an electronic shutter of the first imaging element and a diaphragm amount of an electronic shutter of the second imaging element while maintaining a state in which a ratio between an effective exposure period of the first imaging element and an effective exposure period of the second imaging element is a specific ratio.

2. The medical control device according to claim 1, wherein the circuitry is configured to adjust each of the light amount of the first light and the light amount of the second light while maintaining a state in which a ratio between the light amount of the first light and the light amount of the second light is a specific ratio.

3. The medical control device according to claim 1, wherein the second processing adjusts the diaphragm amount of the electronic shutter of the first imaging element to discard the image information including charges accumulated for each pixel.

4. The medical control device according to claim 1, wherein the second processing is executed when the first captured image and the second captured image are transmitted from the imaging device to the medical control device.

5. The medical control device according to claim 1, wherein the first processing is long-time exposure in which a plurality of fields is set as one field in a pseudo manner.

6. The medical control device according to claim 1, wherein
the imaging element includes
the first imaging element configured to generate the first captured image, and
the second imaging element configured to generate the second captured image,
the second processing is processing of adjusting the diaphragm amount of the electronic shutter of the first imaging element and the diaphragm amount of the electronic shutter of the second imaging element,
in a case where brightness of the first captured image and the second captured image is lowered, the circuitry is configured to reduce the light amount of the first light and the light amount of the second light while maintaining a state in which a ratio between the light amount of the first light and the light amount of the second light is a specific ratio.

7. The medical control device according to claim 1, wherein the first light is excitation light for generating fluorescence from the observation target, and the second light is white light.

8. The medical control device according to claim 1, wherein the light source is configured to emit a plurality of the first light having different wavelength bands, the second processing is processing of adjusting the diaphragm amount of the electronic shutter of the imaging element, and the circuitry is further configured to set, in the second processing, the diaphragm amount of the electronic shutter of the first imaging element to a diaphragm amount corresponding to first light emitted from the light source among the plurality of the first light.

9. The medical control device according to claim 1, wherein the first imaging element and the second imaging element each comprise a complementary metal oxide semiconductor (CMOS) image sensor.

10. The medical control device according to claim 1, wherein the imaging device further comprises a prism configured to separate return light from the observation target and direct a first portion of the return light toward the first imaging element and a second portion of the return light toward the second imaging element.

11. The medical control device according to claim 7, wherein the excitation light is near-infrared excitation light that excites a fluorescent substance comprising indocyanine green.

12. The medical control device according to claim 1, wherein the imaging device is incorporated into a rigid endoscope.

13. The medical control device according to claim 1, wherein the imaging device is incorporated into a flexible endoscope.

14. The medical control device according to claim 1, wherein the imaging device is incorporated into a surgical microscope.

15. A medical observation system comprising:

a light source configured to emit first light and second light having a wavelength band different from a wavelength band of the first light;

an imaging device including a first imaging element and a second imaging element, the imaging device being configured to irradiate an observation target with the first light to capture return light of the first light via the observation target to generate a first captured image, and irradiate the observation target with the second light to capture return light of the second light via the observation target to generate a second captured image; and circuitry configured to control operations of the light source device and the imaging device, the circuitry further configured to control an operation of the light source device and adjust a light amount of the first light and a light amount of the second light, and control an operation of the imaging device, and execute first processing of changing an exposure period of the imaging element, and second processing of discarding image information generated by the imaging element according to light reception in a partial period of the exposure period, wherein the circuitry is further configured to control an increase, after the light amount of the first light and the light amount of the second light decrease to a drive limit value, a diaphragm amount of an electronic shutter of the first imaging element and a diaphragm amount of an electronic shutter of the second imaging element while maintaining a state in which a ratio between an effective exposure period of the first imaging element and an effective exposure period of the second imaging element is a specific ratio.

16. The medical observation system according to claim 15, wherein the first processing is long-time exposure in which a plurality of fields is set as one field in a pseudo manner.

17. The medical observation system according to claim 15, wherein the first light is excitation light for generating fluorescence from the observation target, and the second light is white light.

18. The medical observation system according to claim 15, wherein the imaging device is incorporated into a rigid endoscope.

19. The medical observation system according to claim 15, wherein the imaging device is incorporated into a flexible endoscope.

20. The medical control device according to claim 1, wherein the image information corresponds to a charge accumulated for each pixel by the imaging element.

* * * * *